United States Patent
Offner et al.

(10) Patent No.: US 10,889,802 B2
(45) Date of Patent: Jan. 12, 2021

(54) B-CELL CULTIVATION METHOD

(71) Applicant: Hoffmann-La Roche Inc., Little Falls, NJ (US)

(72) Inventors: Sonja Offner, Penzberg (DE); Friederike Jung, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/144,240

(22) Filed: Sep. 27, 2018

(65) Prior Publication Data

US 2019/0017022 A1    Jan. 17, 2019

Related U.S. Application Data

(63) Continuation of application No. PCT/EP2017/057250, filed on Mar. 28, 2017.

(30) Foreign Application Priority Data

Mar. 30, 2016  (EP) .................................... 16162954

(51) Int. Cl.
*C12N 5/0781* (2010.01)

(52) U.S. Cl.
CPC .... *C12N 5/0635* (2013.01); *C12N 2501/2301* (2013.01); *C12N 2501/231* (2013.01); *C12N 2501/2302* (2013.01); *C12N 2501/2304* (2013.01); *C12N 2501/2306* (2013.01); *C12N 2501/2321* (2013.01); *C12N 2501/25* (2013.01); *C12N 2502/1185* (2013.01); *C12N 2502/30* (2013.01); *C12N 2510/02* (2013.01); *C12N 2525/00* (2013.01)

(58) Field of Classification Search
CPC .......... C12N 5/0635; C12N 2501/2321; C12N 2501/231; C12N 2501/2306; C12N 2501/2304; C12N 2501/2302; C12N 2525/00; C12N 2501/25; C12N 2502/1185; C12N 2502/30; C12N 2510/02; C12N 2501/23
See application file for complete search history.

(56) References Cited

U.S. PATENT DOCUMENTS

| 7,731,969 B1 * | 6/2010 | Tucker ................... C07K 16/00 424/184.1 |
| 7,807,415 B2 | 10/2010 | Groen et al. |
| 2006/0051348 A1 | 3/2006 | Gorlach |
| 2007/0065919 A1 | 3/2007 | Groen et al. |
| 2007/0269868 A1 | 11/2007 | Jensen et al. |

FOREIGN PATENT DOCUMENTS

| WO | 2007/031550 A2 | 3/2007 |
| WO | 2008/045140 A1 | 4/2008 |
| WO | 2008/144763 A2 | 11/2008 |
| WO | 2011/147903 A1 | 12/2011 |
| WO | 2012/178150 A2 | 12/2012 |
| WO | 2012/178150 A3 | 12/2012 |
| WO | 2013/076139 A1 | 5/2013 |
| WO | 2013/092716 A1 | 6/2013 |

OTHER PUBLICATIONS

European Search Report on patentability for European Application No. EP 16 16 2954 completed on Aug. 8, 2017.
International Search Report and Written Opinion for International Application No. PCT/EP2017/057250 completed on May 3, 2017.
Crowe Laboratory: Technical Sheet Name of Cell Line: EL4-B5 Species: Mouse (*Mus musculus*) Type of cell: Mouse thymoma continuous cell line history of the E-4 B5 cells, Dec. 24, 2009 XP055293836, retrieved from the Internet: URL:https://www.kerafast.com/PDF/EL4 Cell Line Information.pdf on Dec. 14, 2018.
Dohmen et al., "Production of recombinant Ig molecules from antigen-selected single B cells and restricted usage of Ig-gene segments by anti-D antibodies" J Immunol Meth 298(1-2):9-20 (Mar. 2005).
Kwekkeboom et al., "An efficient procedure for the generation of human monoclonal antibodies based on activation of human B lymphocytes by a murine thymoma cell line" J Immunol Meth 160(1):117-127 (Jan. 1, 1993).
Masri et al., "Cloning and expression in *E. coli* of a functional Fab fragment obtained from single human lymphocyte against anthrax toxin" Molec Immunol 44:2101-2106 ( 2007).
Seeber et al., "A robust high throughput platform to generate functional recombinant monoclonal antibodies using rabbit B cells from peripheral blood" PLOS One 9(2):e86184-14 (Feb. 4, 2014).
Weber et al., "Combining EL4-B5-based B-cell stimulation and phage display technology for the successful isolation of human anti-Scl-70 autoantibody fragments" J Immunol Meth 278:249-259 ( 2003).
Weitkamp et al., "Generation of recombinant human monoclonal antibodies to rotavirus from single antigen-specific B cells selected with fluorescent virus-like particles" J Immunol Meth 275:223-237 ( 2003)
Zubler et al., "Activated B cells express Receptors for, and proliferate in response to, pure Interleukin2" J Exp Med 160:1170-1183 (Oct. 1984).
Zubler, "Polyclonal B cell responses in the presence of defined filler cells: complementary effects of lipopolysaccharide and anti-immunoglobulin antibodies" Eur J Immunol 14:357-363 ( 1984).
Brinkmann et al., "T Cell-Dependent Differentiation of Human B Cells into IgM, IgG, IgA, or IgE Plasma Cells: High Rate of Antibody Production by IgE Plasma Cells, but Limited Clonal Expansion of IgE Precursors" Cellular Immunology 152(2):323-332 (1993).

(Continued)

*Primary Examiner* — Sean C. Barron
(74) *Attorney, Agent, or Firm* — Jonathan P. Aumais

(57) ABSTRACT

Herein is reported a method for co-cultivating one or more B-cells comprising the step of incubating the one or more B-cells with EL4-B5 cells, whereby the EL4-B5 cells have been obtained/are from a cultivation of EL4-B5 cells that has a cell density of from 600,000 cells/ml up to 1,500,000 cells/ml.

15 Claims, 2 Drawing Sheets

Specification includes a Sequence Listing.

(56) References Cited

OTHER PUBLICATIONS

Leyendeckers et al., "Correlation analysis between frequencies of circulating antigen-specific IgG-bearing memory Bcells and serum titers of antigen-specific IgG" European Journal of Immunology 29:1406-1417 (1999).
Lundgren et al., "Interleukin 4 induces synthesis of IgE and IgG4 in human B cells*" Eur. Journal of Immunology 19(7):1311-1315 (1989).
Matthes et al., "Cytokine mRNA expression during an in vitro response of human B lymphocytes: kinetics of B cell tumor necrosis factor alpha, interleukin (IL)6, IL-10, and transforming growth factor beta 1 mRNAs" Journal of Experimental Medicine 178(2):521-628 (1993).
Steenbakkers et al., "Efficient generation of human anti-cytomegalovirus IgG monoclonal antibodies from preselected antigen-specific B cells" Human Antibodies 4(4):166-173 (1993).
Wen et al., "Limiting dilution assay for human B cells based on their activation by mutant EL4 thymoma cells: total and antimalaria responder B cell frequencies*" Eur. J. Immunol. 17:887-892 (1987).
Wildt et al., "A new method for the analysis and production of monoclonal antibody fragments originating from single human B cells" Journal of Immunological Methods 207(1):61-67 (1997).
Zubler et al., "Mutant EL-4 thymoma cells polyclonally activate murine and human B cells via direct cell interaction" The Journal of Immunology 134(6) (1985).

\* cited by examiner

SEQUENCE LISTING

<160> NUMBER OF SEQ ID NOS: 45

<210> SEQ ID NO 1
<211> LENGTH: 32
<212> TYPE: DNA
<213> ORGANISM: Artificial Sequence
<220> FEATURE:
<223> OTHER INFORMATION: rb-V-kappa-HindIIIs primer

<400> SEQUENCE: 1
gattaagctt atggacayga gggcccccac tc                                32

<210> SEQ ID NO 2
<211> LENGTH: 35
<212> TYPE: DNA

```
<213> ORGANISM: Artificial Sequence
<220> FEATURE:
<223> OTHER INFORMATION: rb-C-kappa-NheIas primer

<400> SEQUENCE: 2
gatcgctagc cctggcaggc gtctcrctct aacag                            35

<210> SEQ ID NO 3
<211> LENGTH: 23
<212> TYPE: DNA
<213> ORGANISM: Artificial Sequence
<220> FEATURE:
<223> OTHER INFORMATION: rb-CH1rev-1 primer

<400> SEQUENCE: 3
gcagggggcc agtgggaaga ctg                                         23

<210> SEQ ID NO 4
<211> LENGTH: 29
<212> TYPE: DNA
<213> ORGANISM: Artificial Sequence
<220> FEATURE:
<223> OTHER INFORMATION: rbVH3-23for3 primer

<400> SEQUENCE: 4
caccatggag actgggctgc gctggcttc                                   29

<210> SEQ ID NO 5
<211> LENGTH: 20
<212> TYPE: DNA
<213> ORGANISM: Artificial Sequence
<220> FEATURE:
<223> OTHER INFORMATION: bcPCR-huCgamma-rev primer

<400> SEQUENCE: 5
cccccagagg tgctcttgga                                             20

<210> SEQ ID NO 6
<211> LENGTH: 20
<212> TYPE: DNA
<213> ORGANISM: Artificial Sequence
<220> FEATURE:
<223> OTHER INFORMATION: bcPCR-FHLC-leader-fw primer

<400> SEQUENCE: 6
atggacatga gggtccccgc                                             20

<210> SEQ ID NO 7
<211> LENGTH: 24
<212> TYPE: DNA
<213> ORGANISM: Artificial Sequence
<220> FEATURE:
<223> OTHER INFORMATION: bcPCR-huCkappa-rev primer

<400> SEQUENCE: 7
gatttcaact gctcatcaga tggc                                        24

<210> SEQ ID NO 8
<211> LENGTH: 45
<212> TYPE: DNA
<213> ORGANISM: Artificial Sequence
<220> FEATURE:
<223> OTHER INFORMATION: bcPCR-hu-HC-10600-SLIC-as primer

<400> SEQUENCE: 8
cagcccagtc tccatggtgg caagcttcct ctgtgttcag tgctg                 45
```

<210> SEQ ID NO 9
<211> LENGTH: 26
<212> TYPE: DNA
<213> ORGANISM: Artificial Sequence
<220> FEATURE:
<223> OTHER INFORMATION: bcPCR-hu-HC-10600-SLIC-s primer

<400> SEQUENCE: 9
ctccaagagc acctctgggg gcacag                                                26

<210> SEQ ID NO 10
<211> LENGTH: 24
<212> TYPE: DNA
<213> ORGANISM: Artificial Sequence
<220> FEATURE:
<223> OTHER INFORMATION: bcPCR-hu-LC-10603-SLIC-s primer

<400> SEQUENCE: 10
gccatctgat gagcagttga aatc                                                  24

<210> SEQ ID NO 11
<211> LENGTH: 38
<212> TYPE: DNA
<213> ORGANISM: Artificial Sequence
<220> FEATURE:
<223> OTHER INFORMATION: bcPCR-hu-LC-10603-SLIC-as primer

<400> SEQUENCE: 11
gcggggaccc tcatgtccat ggtggcaagc ttcctctg                                   38

<210> SEQ ID NO 12
<211> LENGTH: 48
<212> TYPE: DNA
<213> ORGANISM: Artificial Sequence
<220> FEATURE:
<223> OTHER INFORMATION: SLIC-hu-VHuniversal-for primer

<400> SEQUENCE: 12
agcaacagct acaggtgtgc attccgaggt gcagctgktg sagtctgs                        48

<210> SEQ ID NO 13
<211> LENGTH: 45
<212> TYPE: DNA
<213> ORGANISM: Artificial Sequence
<220> FEATURE:
<223> OTHER INFORMATION: SLIC-hu-VH6-for primer

<400> SEQUENCE: 13
agcaacagct acaggtgtgc attcccaggt rcagctgcag sagtc                           45

<210> SEQ ID NO 14
<211> LENGTH: 24
<212> TYPE: DNA
<213> ORGANISM: Artificial Sequence
<220> FEATURE:
<223> OTHER INFORMATION: hu-CH1gamma-rev primer

<400> SEQUENCE: 14
gtccaccttg gtgttgctgg gctt                                                  24

<210> SEQ ID NO 15
<211> LENGTH: 47
<212> TYPE: DNA
<213> ORGANISM: Artificial Sequence
<220> FEATURE:

<223> OTHER INFORMATION: SLIC-huVk2-for primer

<400> SEQUENCE: 15
tagcaacagc tacaggtgtg cattccgatg ttgtgatgac tcagtct					47

<210> SEQ ID NO 16
<211> LENGTH: 47
<212> TYPE: DNA
<213> ORGANISM: Artificial Sequence
<220> FEATURE:
<223> OTHER INFORMATION: SLIC-huVk3-for primer

<400> SEQUENCE: 16
tagcaacagc tacaggtgtg cattccgaaa ttgtgwtgac rcagtct					47

<210> SEQ ID NO 17
<211> LENGTH: 44
<212> TYPE: DNA
<213> ORGANISM: Artificial Sequence
<220> FEATURE:
<223> OTHER INFORMATION: SLIC-huVk5-for primer

<400> SEQUENCE: 17
tagcaacagc tacaggtgtg cattccgaca tcgtgatgac ccag					44

<210> SEQ ID NO 18
<211> LENGTH: 47
<212> TYPE: DNA
<213> ORGANISM: Artificial Sequence
<220> FEATURE:
<223> OTHER INFORMATION: SLIC-huVk7-for primer

<400> SEQUENCE: 18
tagcaacagc tacaggtgtg cattccgaaa ttgtgctgac tcagtct					47

<210> SEQ ID NO 19
<211> LENGTH: 49
<212> TYPE: DNA
<213> ORGANISM: Artificial Sequence
<220> FEATURE:
<223> OTHER INFORMATION: SLIC-huVk8-for primer

<400> SEQUENCE: 19
tagcaacagc tacaggtgtg cattccgawr ttgtgmtgac kcagtctcc					49

<210> SEQ ID NO 20
<211> LENGTH: 47
<212> TYPE: DNA
<213> ORGANISM: Artificial Sequence
<220> FEATURE:
<223> OTHER INFORMATION: SLIC-huVk1long-for primer

<400> SEQUENCE: 20
tagcaacagc tacaggtgtg cattccgaca tccrgwtgac ccagtct					47

<210> SEQ ID NO 21
<211> LENGTH: 47
<212> TYPE: DNA
<213> ORGANISM: Artificial Sequence
<220> FEATURE:
<223> OTHER INFORMATION: SLIC-huVk2longw-for primer

<400> SEQUENCE: 21
tagcaacagc tacaggtgtg cattccgatr ttgtgatgac ycagwct					47

<210> SEQ ID NO 22
<211> LENGTH: 22
<212> TYPE: DNA
<213> ORGANISM: Artificial Sequence
<220> FEATURE:
<223> OTHER INFORMATION: huCk-rev primer

<400> SEQUENCE: 22
acactctccc ctgttgaagc tc                                            22

<210> SEQ ID NO 23
<211> LENGTH: 44
<212> TYPE: DNA
<213> ORGANISM: Artificial Sequence
<220> FEATURE:
<223> OTHER INFORMATION: SLIC-huVl1-for primer

<400> SEQUENCE: 23
tagcaacagc tacaggtgtg cattcccagt ctgtgytgac kcag                    44

<210> SEQ ID NO 24
<211> LENGTH: 44
<212> TYPE: DNA
<213> ORGANISM: Artificial Sequence
<220> FEATURE:
<223> OTHER INFORMATION: SLIC-huVl2-for primer

<400> SEQUENCE: 24
tagcaacagc tacaggtgtg cattcccagt ctgccctgac tcag                    44

<210> SEQ ID NO 25
<211> LENGTH: 44
<212> TYPE: DNA
<213> ORGANISM: Artificial Sequence
<220> FEATURE:
<223> OTHER INFORMATION: SLIC-huVl3-for primer

<400> SEQUENCE: 25
tagcaacagc tacaggtgtg cattcctcct atgagctgay wcag                    44

<210> SEQ ID NO 26
<211> LENGTH: 44
<212> TYPE: DNA
<213> ORGANISM: Artificial Sequence
<220> FEATURE:
<223> OTHER INFORMATION: SLIC-huVl4-for primer

<400> SEQUENCE: 26
tagcaacagc tacaggtgtg cattcccagc ytgtgctgac tcaa                    44

<210> SEQ ID NO 27
<211> LENGTH: 44
<212> TYPE: DNA
<213> ORGANISM: Artificial Sequence
<220> FEATURE:
<223> OTHER INFORMATION: SLIC-huVl5-for primer

<400> SEQUENCE: 27
tagcaacagc tacaggtgtg cattcccags ctgtgctgac tcag                    44

<210> SEQ ID NO 28
<211> LENGTH: 44
<212> TYPE: DNA
<213> ORGANISM: Artificial Sequence
<220> FEATURE:
<223> OTHER INFORMATION: SLIC-huVl6-for primer

<400> SEQUENCE: 28
tagcaacagc tacaggtgtg cattccaatt ttatgctgac tcag    44

<210> SEQ ID NO 29
<211> LENGTH: 44
<212> TYPE: DNA
<213> ORGANISM: Artificial Sequence
<220> FEATURE:
<223> OTHER INFORMATION: SLIC-huVl7-for primer

<400> SEQUENCE: 29
tagcaacagc tacaggtgtg cattcccagr ctgtggtgac tcag    44

<210> SEQ ID NO 30
<211> LENGTH: 44
<212> TYPE: DNA
<213> ORGANISM: Artificial Sequence
<220> FEATURE:
<223> OTHER INFORMATION: SLIC-huVl8-for primer

<400> SEQUENCE: 30
tagcaacagc tacaggtgtg cattcccaga ctgtggtgac ccag    44

<210> SEQ ID NO 31
<211> LENGTH: 44
<212> TYPE: DNA
<213> ORGANISM: Artificial Sequence
<220> FEATURE:
<223> OTHER INFORMATION: SLIC-huVl9-for primer

<400> SEQUENCE: 31
tagcaacagc tacaggtgtg cattcccwgc ctgtgctgac tcag    44

<210> SEQ ID NO 32
<211> LENGTH: 44
<212> TYPE: DNA
<213> ORGANISM: Artificial Sequence
<220> FEATURE:
<223> OTHER INFORMATION: SLIC-huVlambda10-for primer

<400> SEQUENCE: 32
tagcaacagc tacaggtgtg cattcccagg cagggctgac tcag    44

<210> SEQ ID NO 33
<211> LENGTH: 19
<212> TYPE: DNA
<213> ORGANISM: Artificial Sequence
<220> FEATURE:
<223> OTHER INFORMATION: huCl-1-rev primer

<400> SEQUENCE: 33
tctccacggt gctcccttc    19

<210> SEQ ID NO 34
<211> LENGTH: 26
<212> TYPE: DNA
<213> ORGANISM: Artificial Sequence
<220> FEATURE:
<223> OTHER INFORMATION: huIg-PCR-vectorprimer-as

<400> SEQUENCE: 34
ggaatgcaca cctgtagctg ttgcta    26

<210> SEQ ID NO 35
<211> LENGTH: 24

```
<212> TYPE: DNA
<213> ORGANISM: Artificial Sequence
<220> FEATURE:
<223> OTHER INFORMATION: huIg-PCR-vectorprimer-VH-s

<400> SEQUENCE: 35
aagcccagca acaccaaggt ggac                                        24

<210> SEQ ID NO 36
<211> LENGTH: 26
<212> TYPE: DNA
<213> ORGANISM: Artificial Sequence
<220> FEATURE:
<223> OTHER INFORMATION: huIg-PCR-vectorprimer-as kappa

<400> SEQUENCE: 36
ggaatgcaca cctgtagctg ttgcta                                      26

<210> SEQ ID NO 37
<211> LENGTH: 22
<212> TYPE: DNA
<213> ORGANISM: Artificial Sequence
<220> FEATURE:
<223> OTHER INFORMATION: huIg-PCR-vectorprimer-VK-s

<400> SEQUENCE: 37
gagcttcaac aggggagagt gt                                          22

<210> SEQ ID NO 38
<211> LENGTH: 26
<212> TYPE: DNA
<213> ORGANISM: Artificial Sequence
<220> FEATURE:
<223> OTHER INFORMATION: huIg-PCR-vectorprimer-as lambda

<400> SEQUENCE: 38
ggaatgcaca cctgtagctg ttgcta                                      26

<210> SEQ ID NO 39
<211> LENGTH: 19
<212> TYPE: DNA
<213> ORGANISM: Artificial Sequence
<220> FEATURE:
<223> OTHER INFORMATION: huIg-PCR-vectorprimer-VL-s

<400> SEQUENCE: 39
gaagggagca ccgtggaga                                              19

<210> SEQ ID NO 40
<211> LENGTH: 4
<212> TYPE: PRT
<213> ORGANISM: Homo sapiens

<400> SEQUENCE: 40

Glu Val Gln Leu
1

<210> SEQ ID NO 41
<211> LENGTH: 4
<212> TYPE: PRT
<213> ORGANISM: Homo sapiens

<400> SEQUENCE: 41

Gln Val Gln Leu
1
```

```
<210> SEQ ID NO 42
<211> LENGTH: 3
<212> TYPE: PRT
<213> ORGANISM: Homo sapiens

<400> SEQUENCE: 42

Val Ser Ser
1

<210> SEQ ID NO 43
<211> LENGTH: 4
<212> TYPE: PRT
<213> ORGANISM: Homo sapiens

<400> SEQUENCE: 43

Asp Ile Val Met
1

<210> SEQ ID NO 44
<211> LENGTH: 4
<212> TYPE: PRT
<213> ORGANISM: Homo sapiens

<400> SEQUENCE: 44

Asp Ile Gln Met
1

<210> SEQ ID NO 45
<211> LENGTH: 5
<212> TYPE: PRT
<213> ORGANISM: Homo sapiens

<400> SEQUENCE: 45

Lys Leu Glu Ile Lys
1               5
```

B-CELL CULTIVATION METHOD

CROSS REFERENCE TO RELATED APPLICATIONS

This application is a continuation application of International Application No. PCT/EP2017/057250, filed on Mar. 28, 2017, the entire contents of which are incorporated herein by reference, and which claims priority to EP 16162954.8, filed on Mar. 30, 2016.

SEQUENCE LISTING

This application contains a Sequence Listing which has been submitted electronically as a text file in ASCII format and is herein incorporated by reference in its entirety. Said text file, created on Sep. 26, 2018 is named "P33508-US_Seq_Listing.txt" and is 8,638 bytes in size.

FIELD OF THE INVENTION

Herein are reported methods for co-cultivating B-cells with EL4-B5 feeder cells, which have been obtained from a culture of EL4-B5 cells of a certain cell density, obtaining the amino acid sequence of at least the variable domains of a monoclonal antibody secreted by a single B-cell, and for producing the antibody.

BACKGROUND OF THE INVENTION

For obtaining cells secreting monoclonal antibodies the hybridoma technology developed by Koehler and Milstein is widely used. But in the hybridoma technology only a fraction of the B-cells obtained from an immunized experimental animal can be fused and propagated. The source of the B-cells is generally an organ of an immunized experimental animal such as the spleen.

Zubler et al. started in 1984 to develop a different approach for obtaining cells secreting monoclonal antibodies (see e.g. Eur. J. Immunol. 14 (1984) 357-363, J. Exp. Med. 160 (1984) 1170-1183). Therein the B-cells are obtained from the blood of the immunized experimental animal and co-cultivated with murine EL-4 B5 feeder cells in the presence of a cytokine comprising feeder mix. With this methodology up to 50 ng/ml antibody can be obtained after 10-12 days of co-cultivation.

Weitkamp, J-H., et al., (J. Immunol. Meth. 275 (2003) 223-237) report the generation of recombinant human monoclonal antibodies to rotavirus from single antigen-specific B-cells selected with fluorescent virus-like particles. A method of producing a plurality of isolated antibodies to a plurality of cognate antigens is reported in US 2006/0051348. In WO 2008/144763 and WO 2008/045140 antibodies to IL-6 and uses thereof and a culture method for obtaining a clonal population of antigen-specific B cells are reported, respectively. A culture method for obtaining a clonal population of antigen-specific B-cells is reported in US 2007/0269868. Masri et al. (Mol. Immunol. 44 (2007) 2101-2106) report the cloning and expression in *E. coli* of a functional Fab fragment obtained from single human lymphocyte against anthrax toxin. A method for preparing immunoglobulin libraries is reported in WO 2007/031550.

In WO 2011/147903 a single B-cell cultivation method is reported.

In WO 2013/076139 CD40L expressing mammalian cells and their use are reported.

In WO 2013/092716 a rapid method for cloning and expression of cognate antibody variable region gene segments is reported.

In U.S. Pat. No. 7,807,415 methods for producing stable immortalized B-lymphocytes are reported. In EP 0 488 470 methods for the production of antibodies are reported.

Seeber, S., et al. reported a robust high throughput platform to generate functional recombinant monoclonal antibodies using rabbit B-cells from peripheral blood (PLOS One 9 (2014) e86184/-14).

In US 2007/065919 methods of producing stable B-lymphocytes are reported.

In WO 2012/178150 methods for developing antigen-specific antibody-producing cell lines and monoclonal antibodies are reported.

Kwekkeboom, J., et al. reported an efficient procedure for the generation of human monoclonal antibodies based on activation of human B lymphocytes by a murine thymoma cell line (J. Immunol. Meth. 160 (1993) 117-127).

Weber, M., et al, reported combining EL4-B5-based B-cell stimulation and phage display technology for the successful isolation of human anti-Scl-70 autoantibody fragments (J. Immunol. Meth. 278 (2003) 249-259).

Dohmen, S. E., et al., reported about the production of recombinant Ig molecules from antigen-selected single B cells and restricted usage of Ig-gene segments by anti-D antibodies (J. Immunol. Meth. 298 (2005) 9-20).

SUMMARY OF THE INVENTION

Herein is reported a method for the co-cultivation of single deposited B-cells, which can be of any source, with feeder cells in a suitable co-cultivation medium.

The invention is based at least in part on the finding that the EL4-B5 feeder cells used in the co-cultivation can be obtained from a cultivation of EL4-B5 cells that has a cell density of more than 500,000 cells/ml, especially in the range of 600,000 cells/ml up to 1,500,000 cells/ml, i.e. the EL4-B5 cells have been cultivated up to said cell density.

The invention is further based at least in part on the finding that overall the frequency of antigen binding and IgG positive wells amongst all IgG positive wells increases depending on the EL-4-B5 cultivation density at the time of harvest of the EL-4-B5 cells, i.e. if EL-4-B5 cells obtained from EL4-B5 cultivations with higher cell densities at the time of EL-4-B5 cell harvest are used in B-cell co-cultivations the before referred-to increase of frequency can be obtained. This effect was observed when EL4-B5 cells obtained from a cultivation of EL4-B5 cell with a cell density of up to 1,500,000 cells/ml were used in the co-cultivation. That is, using the same concentration of EL-4-B5 cells as before in the co-cultivation results in an increased frequency of antigen binding and IgG positive wells when the EL-4-B5 cells have been cultivated to final cell density of up to 1,500,000 cells/ml.

The individual aspects as reported herein are methods for
i) the isolation of a B-cell or a B-cell clone from a population of B-cells, whereby the isolated B-cell or B-cell clone produces an antibody specifically binding to a target,
ii) the co-cultivation of single deposited B-cells, and
iii) the production of an antibody.

Concomitantly with the methods also the corresponding uses are also encompassed and disclosed.

One aspect as reported herein is a method for co-cultivating one or more B-cells comprising the step of
incubating the one or more B-cells with EL4-B5 cells, whereby the EL4-B5 cells have been obtained/are from a cultivation of EL4-B5 cells that has a (final) cell density of from 600,000 cells/ml up to 1,500,000 cells/ml.

In one embodiment the cultivation of EL4-B5 cells has a (final) cell density of 650,000 cells/ml up to 1,450,000 cells/ml.

In one embodiment the cultivation of EL4-B5 cells has a (final) cell density of 650,000 cells/ml up to 825,000 cells/ml.

In one embodiment the cultivation of EL4-B5 cells has a (final) cell density of 1,400,000 cells/ml up to 1,500,000 cells/ml.

One aspect as reported herein is a method for co-cultivating one or more B-cells comprising the steps of
cultivating EL4-B5 cells to a cell density of from about 600,000 cells/ml to about 1,500,000 cells/ml, and
incubating the one or more B-cells with an aliquot of the EL4-B5 cells of/from the cultivation of the EL4-B5 cells of the previous step, i.e. from the cultivation of EL4-B5 cells that has a cell density of from about 600,000 cells/ml to about 1,500,000 cells/ml.

In one embodiment the cultivation of said EL4-B5 cells is to a (final) cell density of from about 650,000 cells/ml to about 1,450,000 cells/ml.

In one embodiment the cultivation of said EL4-B5 cells is to a (final) cell density of from about 650,000 cells/ml to about 825,000 cells/ml.

In one embodiment the cultivation of said EL4-B5 cells is to a (final) cell density of from about 1,400,000 cells/ml to about 1,500,000 cells/ml.

In one embodiment of all aspects the EL4-B5 cells are irradiated with γ-radiation prior to the addition to the one or more B-cells. The dose of the γ-radiation is a sub-lethal dose. In one embodiment the EL4-B5 cells are harvested when the cultivation of said EL4-B5 has a cell density of from about 600,000 cells/ml to about 1,500,000 cells/ml, the cell density in the harvest is adjusted to a cell density of about $1 \times 10^6$ cells/ml, the cell density adjusted EL4-B5 cell suspension is irradiated with γ-radiation of a dose of 50 Gy, and a respective aliquot of the irradiated EL4-B5 cells is added to the one or more B-cells. In one embodiment the aliquot is about $10^4$ to $10^5$ EL-4-B5 cells per B-cell.

In one embodiment of all aspects the one or more B-cells are incubated with about $10^4$ to $10^5$ EL4-B5 cells per B-cell. In one embodiment of all aspects the one or more B-cells are incubated with about $1 \times 10^4$ to about $5 \times 10^4$ EL4-B5 cells per B-cell. In one embodiment of all aspects the one or more B-cells are incubated with about $2 \times 10^4$ EL4-B5 cells per B-cell. Thus the aliquot of the cultivation of the EL4-B5 cells that is added to the one or more B-cells is about $10^4$ to $10^5$, or about $1 \times 10^4$ to about $5 \times 10^4$, or about $2 \times 10^4$ EL4-B5 cells per B-cell.

In one embodiment of all aspects the incubating is additionally in the presence of a feeder mix.

In one embodiment the feeder mix comprises one or more of
 i) interleukin-1 beta and tumor necrosis factor alpha,
 ii) interleukin-2 (IL-2) and/or interleukin-10 (IL-10),
 iii) *Staphylococcus aureus* strain Cowan's cells (SAC),
 iv) interleukin-21 (IL-21) and optionally interleukine-2 (IL-2),
 v) B-cell activation factor of the tumor necrosis factor family (BAFF),
 vi) interleukin-6 (IL-6),
 vii) interleukin-4 (IL-4), and
 viii) thymocyte cultivation supernatant.

In one embodiment the feeder mix comprises *Staphylococcus aureus* strain Cowan's cells (SAC) and thymocyte cultivation supernatant.

In one embodiment of all aspects the method is for the co-cultivation of one B-cell. In one preferred embodiment the one B-cell is a single deposited B-cell.

In one embodiment of all aspects the incubating is for 5 to 14 days.

One aspect as reported herein is a method for producing an antibody comprising the co-cultivation method as reported herein and thereby producing an antibody.

All aspects (methods and uses) as reported herein comprise the step of
 (individually) co-cultivating/incubating (each single deposited or a pool of) B-cell(s) with feeder cells in a co-cultivation medium, which has been supplemented with a feeder mix.

The result of the co-cultivation is a B-cell clone, i.e. a population of B-cells that are the progeny of a single B-cell.

In one embodiment the methods as reported herein comprise prior to the co-cultivating step the following step:
 depositing those B-cells of a population of B-cells that have been labeled with one to three or one to four fluorescence dyes/fluorophores as single cells.

In one embodiment the methods as reported herein comprise prior to the co-cultivating step the following step:
 depositing those B-cells of a population of B-cells as single cells that have been contacted with one to four antibodies each specifically binding to a different B-cell surface antigen, whereby each antibody is conjugated to a different fluorescent dye, but labeled only with one to four fluorescence dyes.

The labeling is in one embodiment by contacting the B-cell population (sequentially or simultaneously) with one to four fluorescently labeled antibodies. Thereby a labeled B-cell preparation is obtained. Each of the fluorescently labeled antibodies binds to a different B-cell surface marker/target.

The depositing is by introducing the labeled B-cell preparation into a flow cytometer and depositing those cells as single cells that have been labeled with one to four fluorescent labels. As it is possible to incubate the cells with more fluorescent dyes as those which are used for selecting the cells in the cell sorter the cells can be selected for the presence of specific surface markers and (optionally) simultaneously for the absence of other surface markers.

The labeling and single cell deposition is done in order to reduce the complexity of the B-cell population by depleting those B-cells that are not likely to produce an antibody having the intended characteristics. The labeled antibodies bind to a specific polypeptide displayed on the surface of B-cells and, thus, provide for a positive selection label. Likewise it is also possible to select cells that are only labeled with a reduced number of fluorescent dyes compared to the number of labeled antibodies with which the B-cell had been incubated, such as e.g. cells having one fluorescent label out of two (i.e. incubation with two fluorescently label antibodies has been performed but only one thereof binds to the B-cells), or two out of three. Based on the binding/non-binding of the fluorescently labeled antibodies to the individual B-cells of the B-cell population it is possible to identify and separate target B-cells using a microfluidic sorting apparatus. Concomitantly with the selection also the amount of the label can be determined.

In one embodiment the methods as reported herein comprise the step of incubating the population of B-cells in the co-cultivation medium prior to the single cell depositing/deposition. In one embodiment the incubating is at about 37° C. In one embodiment the incubating is for 0.5 to two hours. In one embodiment the incubating is for about one hour. In one preferred embodiment the incubating is at about 37° C. for about one hour.

In one embodiment the methods as reported herein comprise after the depositing step and before the co-cultivating step the step of centrifuging the single cell deposited B-cells. In one embodiment the centrifuging is for about 1 min. to about 30 min. In one embodiment the centrifuging is for about 5 min. In one embodiment the centrifuging is at about 100×g to about 1,000×g. In one embodiment the centrifuging is at about 300×g. In one preferred embodiment the centrifuging is for about 5 min. at about 300×g.

In one embodiment the method for selecting/obtaining a B-cell (clone) comprises the following steps:
- a) labeling the B-cells of a population of B-cells with one to four fluorescent dyes (optionally by incubating the B-cell population with two to four fluorescently labeled antibodies specifically binding to two to four different pre-determined B-cell surface markers),
- b) optionally incubating the cells in co-cultivation medium,
- c) depositing those B-cells of the population of B-cells that have been labeled with one to four fluorescent dyes (and optionally not labeled with the other fluorescent dye(s)) as single cells onto preloaded feeder cells,
- d) optionally centrifuging the single deposited B-cells with the preloaded feeder cells,
- e) (individually) co-cultivating each single deposited B-cell with feeder cells in a co-cultivation medium, which has been supplemented with a feeder mix,
- f) selecting a B-cell clone proliferating and secreting an antibody in step e).

In one embodiment the method for producing an antibody specifically binding to a target comprises the following steps
- a) labeling the B-cells of a population of B-cells with one to four fluorescent dyes (optionally by incubating the B-cell population with two to four fluorescently labeled antibodies specifically binding to two to four different pre-determined B-cell surface markers),
- b) optionally incubating the cells in co-cultivation medium,
- c) depositing those B-cells of the population of B-cells that have been labeled with one to four fluorescent dyes (and optionally not labeled with the other fluorescent dye(s)) as single cells onto preloaded feeder cells,
- d) optionally centrifuging the single deposited B-cells with the preloaded feeder cells,
- e) (individually) co-cultivating each single deposited B-cell with feeder cells in a co-cultivation medium, which has been supplemented with a feeder mix,
- f) selecting a B-cell clone of step e) secreting an antibody,
- g) i) obtaining one or more nucleic acids encoding the secreted antibody's variable domains from the B-cell clone selected in step f),
  - ii) if the B-cell clone is not a human B-cell clone humanizing the variable domains and providing the respective encoding nucleic acids, and
  - iii) introducing the one or more nucleic acids in one or more expression vectors,
- h) cultivating a cell, which has been transfected with the one or more expression vectors of step g), and recovering the antibody from the cell or the cultivation supernatant and thereby producing the antibody.

In one embodiment the method for producing an antibody comprising the following steps
- a) labeling the B-cells of a population of B-cells with one to four fluorescent dyes (optionally by incubating the B-cell population with two to four fluorescently labeled antibodies specifically binding to two to four different pre-determined B-cell surface markers),
- b) optionally incubating the cells in co-cultivation medium,
- c) depositing those B-cells of a population of B-cells that have been labeled with one to four fluorescent dyes (and optionally not labeled with the other fluorescent dye(s)) as single cells onto preloaded feeder cells,
- d) optionally centrifuging the single deposited B-cells with the preloaded feeder cells,
- e) (individually) co-cultivating each single deposited B-cell with feeder cells in a co-cultivation medium, which has been supplemented with a feeder mix,
- f) determining the binding specificity of the antibodies secreted in the cultivation medium of the individual B-cells,
- g) obtaining one or more nucleic acids encoding the secreted antibody's variable domains from the B-cell clone by a reverse transcriptase PCR and nucleotide sequencing, (and thereby obtaining a monoclonal antibody variable light and heavy chain domain encoding nucleic acid,)
- h) if the B-cell is a non-human B-cell humanizing the variable light and heavy chain domain and providing a nucleic acid encoding the humanized variable domains,
- i) introducing the monoclonal antibody variable light and heavy chain variable domain encoding nucleic acid in one or more expression vectors for the expression of an (human or humanized) antibody,
- j) introducing the expression vector(s) in a cell,
- k) cultivating the cell and recovering the antibody from the cell or the cell culture supernatant and thereby producing the antibody.

In one embodiment the obtaining one or more nucleic acids encoding the secreted antibody's variable domains from the B-cell clone comprises the following steps:
- extracting total RNA from the antibody-producing B-cell clone,
- performing a single stranded cDNA synthesis/reverse transcription of the extracted polyA$^+$ mRNA,
- performing a PCR with a set of species specific primer,
- optionally removal of the PCR primer/purification of the PCR product,
- optionally sequencing of the PCR product.

In one embodiment the introducing the monoclonal antibody variable light and/or heavy chain variable domain encoding nucleic acid in an expression vector for the expression of an (human or humanized) antibody comprises the following steps:
- T4 polymerase incubation of the variable light and heavy chain variable domain,
- linearization and amplification of the expression vector,
- T4 polymerase incubation of the amplified expression vector,
- sequence and ligation independent cloning of the variable domain encoding nucleic acid into the amplified expression vector, and
- preparation of the vector(s) from pool of vector transformed *E. coli* cells.

In one embodiment of all aspects the method comprises immediately prior to the labeling step the following step:
incubating the population of B-cells with (target) antigen, which is immobilized on a solid surface, and recovering (only) B-cells bound to the immobilized antigen.

In one embodiment of all aspects the population of B-cells is a non-human animal B-cell population. In one embodiment the B-cell population is a mouse B-cell population, or a hamster B-cell population, or a rabbit B-cell population. In one preferred embodiment the B-cell population is a rabbit B-cell population.

In one embodiment of all aspects the population of B-cells is obtained from the blood of a non-human animal 4 days after the immunization. In one embodiment the population of B-cells is obtained from the blood of a non-human animal of from 4 days up to at most 13 days after immunization.

In one embodiment the B-cell population is a human B-cell population.

In one embodiment of all aspects the population of B-cells is obtained from blood by density gradient centrifugation.

In one embodiment of all aspects the B-cells are mature B-cells.

In one embodiment of all aspects the single cells are deposited (individually) into the wells of a multi-well plate.

In one embodiment of all aspects the feeder mix is natural thymocyte cultivation supernatant (TSN) or a synthetic feeder mix. In one embodiment the thymocyte cultivation supernatant is obtained from thymocytes of the thymus gland of a young animal.

In one embodiment of all aspects the feeder mix is a synthetic feeder mix. In one embodiment the synthetic feeder mix comprises
i) interleukin-1 beta and tumor necrosis factor alpha, and/or
ii) interleukin-2 (IL-2) and/or interleukin-10 (IL-10), and/or
iii) *Staphylococcus aureus* strain Cowan's cells (SAC), and/or
iv) interleukin-21 (IL-21) and optionally interleukine-2 (IL-2), and/or
v) B-cell activation factor of the tumor necrosis factor family (BAFF), and/or
vi) interleukin-6 (IL-6), and/or
vii) interleukin-4 (IL-4).

In one embodiment of all aspects the feeder cells are murine EL-4 B5 cells.

In one embodiment the feeder cells are murine EL-4 B5 cells and the feeder mix comprises IL-1ß, TNF-α, IL-10 and one or more selected from IL-21, SAC, BAFF, IL-2, IL-4, and IL-6.

In one embodiment the feeder cells are murine EL-4 B5 cells and the feeder mix comprises IL-1ß, TNF-α, IL-10, SAC and IL-2.

In one embodiment of all aspects the B-cell population is a rabbit B-cell population and the feeder cells are murine EL-4 B5 cells and feeder mix is thymocyte cultivation supernatant.

In one embodiment of all aspects the B-cell population is a rabbit B-cell population and the feeder cells are murine EL-4 B5 cells and the feeder mix is consisting of IL-1ß, TNF-α, and any two of IL-2, IL-6 and IL-10.

In one embodiment of all aspects the B-cell population is a rabbit B-cell population and the feeder cells are murine EL-4 B5 cells and the feeder mix is consisting of IL-1ß, TNF-α, IL-6 and IL-10.

In one embodiment of all aspects the B-cell population is a rabbit B-cell population and the feeder cells are murine EL-4 B5 cells and the feeder mix comprises IL-1ß, TNF-α, IL-10, SAC and IL-2 or IL-6.

In one embodiment of all aspects the B-cell population is a rabbit B-cell population and the feeder cells are murine EL-4 B5 cells and the feeder mix comprises IL-1ß, TNF-α, IL-21 and at least one of IL-2, IL-10 and IL-6.

In one embodiment of all aspects the B-cell population is a rabbit B-cell population and the feeder cells are rabbit CD40L-expressing CHO cells. In one embodiment the feeder mix comprises IL-2 and IL-21 and optionally IL-6.

In one embodiment of all aspects the antibody is a monoclonal antibody.

In one embodiment of all aspects the deposited cells are labeled with one or four fluorescence dyes and the incubation is with two to four fluorescently labeled antibodies.

In one embodiment of all aspects the labeling of the B-cells of the population of B-cells results in labeling of 0.1% to 2.5% of the cells of the (total) B-cell population.

In one embodiment of all aspects the labeling is of B-cell surface IgG.

In one preferred embodiment of all aspects the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG$^+$IgM$^-$-B-cells).

In one preferred embodiment of all aspects the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG$^+$IgM$^-$-B-cells), whereby the population of B-cells has been incubated with (target) antigen, which is immobilized on a solid surface, and (only) B-cells bound to the immobilized antigen have been recovered and subjected to the incubation with the fluorescently labeled antibodies.

In one embodiment of all aspects the B-cell population is a rabbit B-cell population and the incubation is with a fluorescently labeled anti-IgG antibody (the labeling is of cell surface IgG) and the selection is of cells positive for cell surface IgG (results in single cell deposition of IgG$^+$-B-cells).

In one embodiment of all aspects the B-cell population is a rabbit B-cell population and the incubation is with a fluorescently labeled anti-CD138 antibody (the labeling is of cell surface CD138) and the selection is of cells positive for cell surface CD138 (results in single cell deposition of CD138$^+$-B-cells).

In one embodiment of all aspects the B-cell population is a rabbit B-cell population and the incubation is with a fluorescently labeled anti-IgG antibody and a fluorescently labeled anti-CD138 antibody (the labeling is of cell surface IgG and cell surface CD138) and the selection is of cells positive for cell surface IgG and also positive for cell surface CD138 (results in single cell deposition of IgG$^+$CD138$^+$-B-cells).

In one preferred embodiment of all aspects the B-cell population is a rabbit B-cell population and the incubation is with a fluorescently labeled anti-IgG antibody, a fluorescently labeled anti-IgM antibody and optionally a fluorescently labelled anti-human IgG light chain antibody in case of human transgenic rabbit (the labeling is of cell surface IgG, cell surface IgM and optionally cell surface human IgG light chain) and the selection is of cells positive for cell surface IgG, negative for cell surface IgM and optionally positive for cell surface human IgG light chain (results in single cell deposition of IgG+IgM−-B-cells (optionally IgG+IgM−huIgGLC+-B-cells).

In one embodiment of all aspects the co-cultivating is in a co-cultivation medium comprising RPMI 1640 medium supplemented with 10% (v/v) FCS, 1% (w/v) of a 200 mM glutamine solution that comprises penicillin and streptomycin, 2% (v/v) of a 100 mM sodium pyruvate solution, and 1% (v/v) of a 1 M 2-(4-(2-hydroxyethyl)-1-piperazine)-ethane sulfonic acid (HEPES) buffer. In one embodiment the co-cultivation medium further comprises 0.05 mM beta-mercaptoethanol.

In one embodiment the animal is an experimental animal. In one embodiment the experimental animal is selected from mouse, hamster, and rabbit. In one embodiment the experimental animal is a rabbit.

DEFINITIONS

Figure 1:
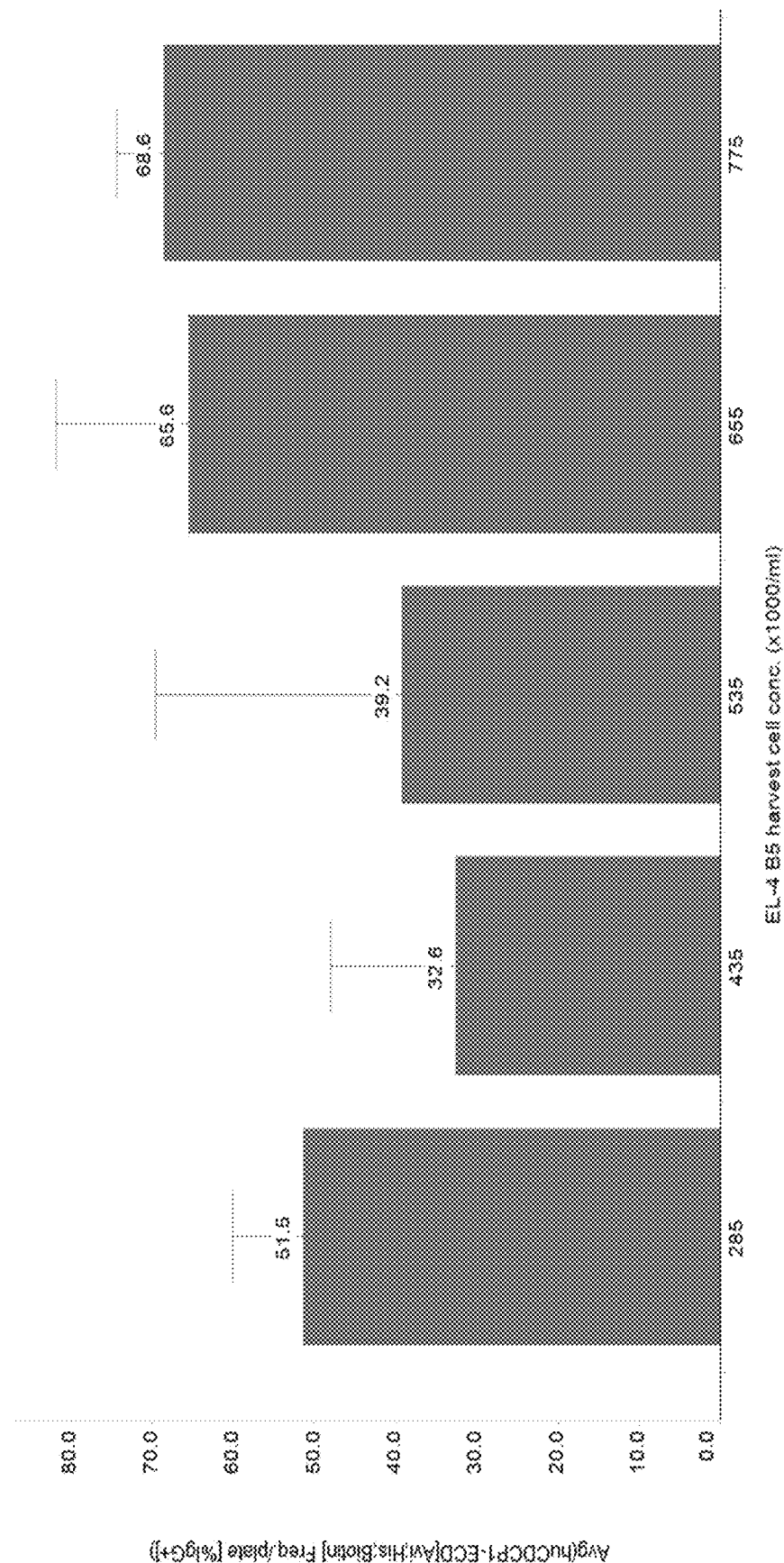
FIG. 1 Average frequency of antigen-specific IgG positive wells per IgG positive wells.

"Affinity" refers to the strength of the total sum of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (kd). Affinity can be measured by common methods known in the art, including those described herein. Specific illustrative and exemplary embodiments for measuring binding affinity are described in the following.

The term "amino acid" as used within this application denotes the group of carboxy α-amino acids, which directly or in form of a precursor can be encoded by a nucleic acid. The individual amino acids are encoded by nucleic acids consisting of three nucleotides, so called codons or base-triplets. Each amino acid is encoded by at least one codon. This is known as "degeneration of the genetic code". The term "amino acid" as used within this application denotes the naturally occurring carboxy a-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "antibody" herein is used to denote naturally occurring antibodies including their naturally occurring structural variants.

For example, native (human, mouse, rat, rabbit) IgG antibodies are heterotetrameric glycoproteins with a molecular weight of about 150,000 Dalton. Native IgG antibodies are composed of two identical light chains and two identical heavy chains comprising inter- and intra-chain disulfide bonds, so that all four chains are covalently linked to each other. From N- to C-terminus, each heavy chain has a variable region (VH), also called a variable heavy chain domain or a heavy chain variable domain, followed by three constant domains (CH1, CH2, and CH3), whereby a flexible hinge region is located between the first and the second constant domain. The heavy chain of an antibody may be assigned to one of five types, called IgA, IgD, IgE, IgG and IgM, depending on their sequence and domain structure ("class" of an antibody). Several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. Similarly, from N- to C-terminus, each light chain has a variable region (VL), also called a variable light chain domain or a light chain variable domain, followed by a constant light chain domain (CL). The light chain of an antibody may be assigned to one of two types, called kappa (κ) and lambda (λ), based on the amino acid sequence of its constant domain.

For example, native (camelid, i.e. from Camelidae, sub-order Tylopoda, which includes camels, dromedaries and llamas) heavy-chain only antibodies (VHH antibodies) do not comprise a classical CH1 domain as found in conventional IgG heavy chains, and, thus, are expressed as VHH domains fused directly to the hinge-CH2-CH3 domains of an antibody. The variable region sequences from llama derived VHH antibodies, for example, are similar to sequences in the human VH3 family of variable domains (Schroeder et al., Int. Immunol. 2 (1989) 41-50). Compared to antibodies of the IgG type the CDR3 domain amino acid sequence in L. llama VHH domains is longer on average than most CDR3 domains of classical IgG type antibodies comprising heavy and light chains. Alike classical IgG antibodies the position of the CDRs in VHH antibodies can be determined by methods well known in the art (see e.g. U.S. Pat. No. 5,637,677). Residues 11, 37, 44, 45 and 47 are important for the formation of the chain interface (see e.g. WO 99/42077).

An "antibody fragment" refers to a molecule other than an intact antibodies (IgG/VHH=four chain/two chain) comprising only a portion of an intact antibody and that binds to the same antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); single domain antibodies; and multispecific antibodies formed from antibody fragments.

The term "cell" includes both prokaryotic cells, which are used for propagation of plasmids, and eukaryotic cells, which are used for the expression of a nucleic acid. In one embodiment the eukaryotic cell is a mammalian cell. In one embodiment the mammalian cell is a CHO cell, optionally a CHO K1 cell (e.g. a ATCC CCL-61 or DSM ACC 110), or a CHO DG44 cell (also known as CHO-DHFR[−], e.g. a DSM ACC 126), or a CHO XL99 cell, a CHO-T cell (see e.g. Morgan, D., et al., Biochemistry 26 (1987) 2959-2963), or a CHO-S cell, or a Super-CHO cell (Pak, S. C. O., et al. Cytotechnol. 22 (1996) 139-146), or BHK cell, or a NS0 cell, or a Sp2/0 cell, or a HEK 293 cell, or a HEK 293 EBNA cell, or a PER.C6® cell, or a COS cell. If these cells are not adapted to growth in serum-free medium or in suspension an adaptation prior to the use in the current method can be performed. As used herein, the expression "cell" includes the subject cell and its progeny. Thus, the words "transformant" and "transformed cell" include the primary subject cell and cultures derived there from without regard for the number of transfers or sub-cultivations. It is also understood that all progeny may not be precisely identical in DNA content, due to deliberate or inadvertent mutations. Variant progeny that have the same function or biological activity as screened for in the originally transformed cell are included.

The term "clone" denotes a population of dividing and antibody secreting B-cells arising from/originating from a single B-cell. Thus, a B-cell clone is a homogeneous population of B-cells and produces a monoclonal antibody.

The term "cognate pair of antibody variable domains" denotes a pair of antibody variable domains that is obtained from a single antibody secreting B-cell (clone), i.e. which has been generated as pair during the immune response of a mammal due to the contact with an immunogenic molecule or which have been assembled randomly during a display approach.

The term "experimental animal" denotes a non-human animal. In one embodiment the experimental animal is selected from rat, mouse, hamster, rabbit, camel, llama, non-human primates, sheep, dog, cow, chicken, amphibians, sharks and reptiles. In one embodiment the experimental animal is a rabbit.

The term "expression" as used herein refers to transcription and/or translation and secretion processes occurring within a cell. The level of transcription of a nucleic acid sequence of interest in a cell can be determined on the basis of the amount of corresponding mRNA that is present in the cell. For example, mRNA transcribed from a sequence of interest can be quantified by qPCR or RT-PCR or by Northern hybridization (see Sambrook, et al., Molecular Cloning: A Laboratory Manual, Second Edition, Cold Spring Harbor Laboratory Press, Cold Spring Harbor, N.Y. (1989)). Polypeptides encoded by a nucleic acid can be quantified by various methods, e.g. by ELISA, by assaying the biological activity of the polypeptide, or by employing assays that are independent of such activity, such as Western blotting or radioimmunoassay, using immunoglobulins that recognize and bind to the polypeptide (see Sambrook, et al., (1989), supra).

To a person skilled in the art procedures and methods are well known to convert an amino acid sequence, e.g. of a polypeptide, into a corresponding nucleic acid sequence encoding this amino acid sequence and vice versa. Therefore, a nucleic acid is characterized by its nucleic acid sequence consisting of individual nucleotides and likewise by the amino acid sequence of a polypeptide encoded thereby.

An "expression cassette" denotes a construct that contains the necessary regulatory elements, such as promoter and polyadenylation site, for expression of at least the contained nucleic acid in a cell.

Expression can be performed either as transient expression or a stable expression. Antibodies are in general secreted into the cultivation medium by the cell producing it. Therefore non-mature antibody chains contain an N-terminal extension (also known as the signal sequence), which is necessary for the transport/secretion of the antibody through the cell wall into the extracellular medium. In general, the signal sequence for recombinant production of an antibody can be derived from any gene encoding a secreted polypeptide. If a heterologous signal sequence is used, it should be one that is recognized and processed (i.e. cleaved by a signal peptidase) by the host cell. For secretion in yeast for example the native signal sequence of a heterologous gene to be expressed may be substituted by a homologous yeast signal sequence derived from a secreted gene, such as the yeast invertase signal sequence, alpha-factor leader (including Saccharomyces, Kluyveromyces, Pichia, and Hansenula α-factor leaders, the second described in U.S. Pat. No. 5,010,182), acid phosphatase signal sequence, or the C. albicans glucoamylase signal sequence (EP 0 362 179). In mammalian cells the native signal sequence is satisfactory, although other mammalian signal sequences may be suitable, such as signal sequences from other secreted polypeptides of the same or related species as well as viral secretory signal sequences, for example, the herpes simplex glycoprotein D signal sequence. The DNA fragment encoding for such a pre-segment is ligated in frame, i.e. operably linked, to the DNA fragment encoding an antibody chain.

The term "expression machinery" denotes the sum of the enzymes, cofactors, etc. of a cell that is involved in the steps of gene expression beginning with the transcription step of a nucleic acid or gene (i.e. also called "gene expression machinery") to the post-translational modification of the polypeptide encoded by the nucleic acid. The expression machinery e.g. comprises the steps of transcription of DNA into pre-mRNA, pre-mRNA splicing to mature mRNA, translation into a polypeptide of the mRNA, and post translational modification of the polypeptide.

An "expression plasmid" or "expression vector" is a nucleic acid providing all required elements for the expression of the comprised structural gene(s) in a host cell. Typically, an expression plasmid/vector comprises a prokaryotic plasmid propagation unit, e.g. for E. coli, comprising an origin of replication, and a selectable marker, a eukaryotic selection marker, and one or more expression cassettes for the expression of the structural gene(s) of interest each comprising a promoter, a structural gene, optionally a transcription terminator and a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "feeder mix" denotes a combination of different additives, such as growth factors, cytokines and/or further proteins promoting the activation and/or survival of B-cells and/or antibody secretion. The feeder mix can be a natural feeder mix, e.g. obtained from the cultivation supernatant of thymocytes (TSN), which is a non-defined combination of cytokines. Alternatively the feeder mix can be a synthetic feeder mix, which is a defined combination of different recombinantly produced or chemically synthesized additives, such as growth factors, cytokines and/or further proteins promoting the activation and/or survival of B-cells and/or antibody secretion.

The terms "host cell", "host cell line", and "host cell culture" are used interchangeably and refer to cells into which exogenous nucleic acid has been introduced, including the progeny of such cells. Host cells include "transformants" or "transfectants" and "transformed cells" and "transfected cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is an antibody, which possesses an amino acid sequence that corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

An "individual" or "subject" is a vertebrate. In one embodiment the vertebrate is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. In other embodiments the individual or subject is a rabbit.

The term "labeling" denotes a process for determining the presence or absence of a surface marker, which can be determined by binding/non-binding of a specifically binding and labeled anti-surface marker antibody to a cell. Thus, the presence of a surface marker is determined e.g. in the case of a fluorescence label by the occurrence of a fluorescence whereas the absence of a surface marker is determined by the absence of a fluorescence after incubation of a cell or a population of cells with the respective specifically binding and labeled anti-surface marker antibody.

The term "monoclonal antibody" as used herein refers to an antibody obtained from a population of substantially homogeneous antibodies produced by a single cell clone, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method.

For example, the monoclonal antibodies to be used in accordance with the present invention may be made by a variety of techniques, including but not limited to methods utilizing transgenic animals containing all or part of the human immunoglobulin loci, such methods and other exemplary methods for making monoclonal antibodies being described herein.

The terms "nucleic acid" and "nucleic acid sequence" denote a polymeric molecule consisting of individual nucleotides (also called bases) a, c, g, and t (or u in RNA), for example to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid/vector, or the chromosome of a host cell. A nucleic acid is characterized by its nucleic acid sequence consisting of individual nucleotides.

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as a secretory leader and a polypeptide, contiguous and in (reading) frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. A translation stop codon is operably linked to an exonic nucleic acid sequence if it is located at the downstream end (3' end) of the coding sequence such that translation proceeds through the coding sequence to the stop codon and is terminated there. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

A "structural gene" denotes the region of a gene without a signal sequence, i.e. the coding region.

The term "specifically binding" and grammatical equivalents thereof denote that the antibody binds to its target with a dissociation constant (KD) of $10^{-7}$ M or less, in one embodiment of from $10^{-8}$ M to $10^{-13}$ M, in a further embodiment of from $10^{-9}$ M to $10^{-13}$ M. The term is further used to indicate that the antibody does not specifically bind to other biomolecules present, i.e. it binds to other biomolecules with a dissociation constant (KD) of $10^{-6}$ M or more, in one embodiment of from $10^{-6}$ M to 1 M.

A "transfection plasmid/vector" is a nucleic acid (also denoted as nucleic acid molecule) providing all required elements for the expression of the in the transfection plasmid/vector comprised coding nucleic acids/structural gene(s) in a host cell. A transfection plasmid/vector comprises a prokaryotic plasmid propagation unit, e.g. for E. coli, in turn comprising a prokaryotic origin of replication, and a nucleic acid conferring resistance to a prokaryotic selection agent, further comprises the transfection plasmid/vector one or more nucleic acid(s) conferring resistance to an eukaryotic selection agent, and one or more nucleic acid encoding a polypeptide of interest. The nucleic acids conferring resistance to a selection agent and the nucleic acid(s) encoding a polypeptide of interest are placed each within an expression cassette, whereby each expression cassette comprises a promoter, a coding nucleic acid, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "variable region" or "variable domain" refers to the region of an antibody heavy or light chain that is involved in the binding of the antibody to its antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J., et al., Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "young animal" denotes an animal before sexual maturity occurs. A young hamster, for example, is of an age of less than 6 weeks, especially less than 4 weeks. A young mouse, for example, is of an age of less than 8 weeks, especially less than 5 weeks.

DETAILED DESCRIPTION OF THE INVENTION

The current invention is based at least in part on the finding that the cell density of the cultivation from which the EL4-B5 feeder cells that are used in a co-cultivation with B-cells are taken has an influence on the frequency (i.e. relative number) of B-cells clones obtained in the co-cultivation of B-cells and EL-4-B5 feeder cells that secrete an antigen-specific antibody. This finding is surprising as the art teaches that a maximum cell density of EL4-B5 cells of 1,000,000 cells/ml in sole EL-4 B5 cultivations shall not be exceeded. It has been found that this is not the case and that even higher cell densities can be used which allows for a more efficient production of the EL4-B5 cells, i.e. the number of cultivations is reduced as a higher cell density can be used without changing the number of EL4-B5 cells employed in the co-cultivation.

The current invention is based at least in part on the finding that overall the frequency of antigen binding and IgG positive wells amongst all IgG positive wells increases when the EL-4 B5 cells used in the co-cultivation have been obtained from a cultivation with EL-4 B5 cell densities higher than published (i.e. higher than 500,000 cell/ml) at the time of harvest of the EL-4-B5 cells are employed. This effect was observed up to a cell density of 1,500,000 cells/ml.

Immunization

For the generation of therapeutic antibodies either a non-human animal is immunized with the therapeutic target (either alone or in combination with an immunogenic stimulus) to elicit an immune response or synthetic approaches, such as phage display libraries are used. If a transgenic animal (i.e. having a human immune system) or a human phage display library is used human antibodies are obtained.

Otherwise non-human animal antibodies are obtained that will be humanized thereafter. A rare possibility to obtain potential therapeutic antibodies is from the blood of a human being that has recovered from a disease.

Often non-human animals, such as mice, rabbits, hamster and rats, are used as animal model for evaluating antibody based therapies. Therefore, it is normally required to provide cross-reactive antibodies binding to the non-human animal antigen as well as to the human antigen.

In the method as reported herein B-cells obtained from any source e.g. human, mouse, hamster or rabbit, can be used. Depending on the source of the B-cell the feeder cells and the feeder mix are adjusted/chosen.

In case of a rabbit B-cell the feeder cell is either an EL4-B5 cell or a mammalian cell, such as a CHO cell or a BHK cell or a HEK cell, expressing rabbit CD40L. In one embodiment the rabbit is selected from New Zealand White (NZW) rabbits, Zimmermann-rabbits (ZIKA), Alicia-mutant strain rabbits, basilea mutant strain rabbits, transgenic rabbits with a human immunoglobulin locus, rbIgM knock-out rabbits, and cross-breeding thereof.

In case of a human B-cell the feeder cell is either an EL4-B5 cell or a mammalian cell, such as a CHO cell or a BHK cell or a HEK cell, expressing human CD40L.

In case of a murine B-cell the feeder cell is either an EL4-B5 cell or a mammalian cell, such as a CHO cell or a BHK cell or a HEK cell, expressing mouse CD40L. In one embodiment the mouse is an NMRI-mouse or a balb/c-mouse.

In case of a hamster B-cell the feeder cell is either an EL4-B5 cell or a mammalian cell, such as a CHO cell or a BHK cell or a HEK cell, expressing hamster CD40L. In one embodiment the hamster is selected from Armenian hamster (*Cricetulus migratorius*), Chinese hamster (*Cricetulus griseus*), and Syrian hamster (*Mesocricetulus auratus*). In a preferred embodiment the hamster is the Armenia hamster.

Source and Isolation of B-Cells

The blood provides a high diversity of antibody producing B-cells. The therefrom obtained B-cell clones secrete antibodies that have almost no identical or overlapping amino acid sequences within the CDRs, thus, show a high diversity.

In one embodiment B-cells, e.g. from the blood, are obtained of from 4 days after immunization until at most 14 days after immunization or the most recent boost of the non-human animal. This time span allows for a high flexibility in the method as reported herein. In this time span it is likely that the B-cells providing for the most affine antibodies migrate from spleen to blood (see e.g. Paus, D., et al., JEM 203 (2006) 1081-1091; Smith, K. G. S., et al., The EMBO J. 16 (1997) 2996-3006; Wrammert, J., et al., Nature 453 (2008) 667-672).

B-cells from the blood, e.g. of a non-human animal or from human blood, may be obtained with any method known in the art. For example, density gradient centrifugation (DGC) or red blood cell lysis (lysis) can be used. Density gradient centrifugation compared to hypotonic lysis provides for a higher overall yield, i.e. number of B-cell clones. Additionally from the cells obtained by density gradient centrifugation a larger number of cells divides and grows in the co-cultivation step. Also the concentration of secreted antibody is higher compared to cells obtained with a different method. Therefore, in one embodiment the providing of a population of B-cells is by density gradient centrifugation.

Alternatively the B-cells can be obtained from spleen or other secondary immunological organs like lymph nodes or Peyers Patches.

Selection Steps Prior to Co-Cultivation

B-cells producing antibodies that specifically bind an antigen can be enriched from peripheral blood mononuclear cells (PBMCs). Thus, in one embodiment of all methods as reported herein the B-cell population is enriched from peripheral blood mononuclear cells (PBMCs).

In one embodiment of all methods as reported herein the PBMCs are depleted of macrophages. This is especially advantageous for B-cells of rabbit origin for the co-cultivation step.

Macrophages can be depleted from PBMCs by adhesion to the surface of the cell culture plate (see pre-incubation step).

Incubating the population of B-cells in co-cultivation medium prior to the single cell depositing can increase the total number of antibody secreting cells obtained after the single cell depositing compared to a single cell depositing directly after the isolation and optional enrichment of the population of B-cells from the blood of a non-human animal (in one embodiment the non-human animal is a rabbit). Specifically the incubating is at about 37° C. for about one hour in EL-4 B5 medium, e.g. using a cell culture incubator.

In one embodiment of the methods as reported herein the cells are from a protein-immunized animal and are depleted of macrophages prior to the labeling.

Cells not producing an antibody binding the antigen or, likewise, cells producing an antibody binding to the antigen can be reduced or enriched, respectively, by using a panning approach. Therein the respective antigen is presented attached to a surface and cells binding thereto are selectively enriched in the cell population in case the bound cells are processed further, or reduced in the cell population in case the cells remaining in solution are processed further.

The method as reported herein comprises in one embodiment prior to the single cell depositing a selecting step in which B-cells producing specific and/or non-cross-reactive antibodies are selected based on cell surface markers and fluorescence activated cell sorting/gating. In one embodiment mature B-cells are sorted/enriched/selected. For selection of B-cells from different non-human animal species different cell surface markers can be used.

With the labeling of non-target cell populations and non-specifically binding lymphocytes it is possible to selectively deplete these cells. In this depletion step only a partial depletion can be achieved. Albeit the depletion is not quantitative it reduces or even eliminates the number of interfering cells in the succeeding fluorescence labeling of the remaining cells. By a single cell depositing of mature B-cells (memory B-cells, affinity matured plasmablasts and plasma cells) by fluorescence activated cell sorting using the labeling a higher number of $IgG^+$-wells/cell clones can be obtained in the co-cultivation step.

Different cell populations can be labeled by using different surface markers such as $CD3^+$-cells (T-cells), $CD19^+$-cells (B-cells), $IgM^+$-cells (mature naive B-cells), $IgG^+$-cells (mature B-cells), $CD38^+$-cells (e.g. plasmablasts), and $IgG^+$ $CD38^+$-cells (pre-plasma cells).

Immuno-fluorescence labeling for selection of mature $IgG^+$-B-cells, such as memory B-cells, plasmablasts, and plasma cells, is available. For a selection or enrichment of B-cells the cells are either single labeled, or double labeled, or triple labeled.

TABLE

Immuno-fluorescence labeling for the determination of mature mouse-(A-J), hamster-(K) and rabbit (L-N)-B-cells.

| B-cell origin | sorting of B-cells with | fraction of all viable cells (%) |
|---|---|---|
| mouse | $IgG^+CD19^+$ | 0.5 ± 0.2 n = 14 |
| mouse | $IgG^+CD38^+$ | 0.8 ± 0.5 n = 9 |
| mouse | $IgG^+CD138^+$ | 0.06 ± 0.07 n = 6 |
| mouse | $IgG^-CD138^+$ | 0.6 ± 0.5 n = 6 |
| mouse | $IgG^+CD27^+$ | 0.1 ± 0.1 n = 8 |
| mouse | $CD27^+CD138^+$ | 1.5 ± 0.5 n = 2 |
| mouse | $CD27^+IgG^+CD3^-$ | 0.10 ± 0.04 n = 3 |
| mouse | $CD3^-CD27^+$ | 1.33 n = 1 |
| mouse | $IgG^+CD268^+$ | 0.8 n = 1 |
| mouse | $CD38^+CD3^-$ | 12 ± 7 n = 2 |
| hamster | $IgG^+IgM^-$ | 0.6 ± 0.1 n = 15 |
| rabbit | $IgG^+$ | 0.6 ± 0.2, n = 5 |
| rabbit | $IgG^+IgM^-$ | 0.4 ± 0.2, n = 2 |
| rabbit | $IgG^+CD138^+$ | 0.3 ± 0.1, n = 5 |

In one embodiment the methods comprise the step of depleting the B-cell population of macrophages and enriching of B-cells of the B-cell population secreting antibody specifically binding a target antigen.

Single Cell Depositing

The method as reported herein comprises the step of depositing the B-cells of a B-cell population as single cells.

In one embodiment of all methods as reported herein the depositing as single cells is by fluorescence activated cell sorting (FACS). The surface marker used for the labeling required for the FACS single cell depositing can be with the specific marker combination as outlined herein.

An additional centrifugation step after the single cell depositing and prior to the co-cultivation can increase the number of antibody secreting cells and the amount of the secreted IgG.

In one embodiment of all methods as reported herein the method comprises the step of centrifuging the single deposited cells prior to the co-cultivation. In one preferred embodiment the centrifuging is for 5 min. at 300×g.

Co-Cultivation

The single deposited B-cells are co-cultivated with murine EL-4-B5 feeder cells in the presence of a feeder mix.

As outlined above an increase in the yield in the co-cultivation step (number of $IgG^+$-wells/cell clones as well as IgG-concentration) and also an enrichment or isolation of mature $IgG^+$-B-cell from PBMCs can be achieved by suitable immuno fluorescence labeling.

The immuno-fluorescence labeling used for B-cells obtained from the blood of an experimental non-human animal can also be used for the labeling of B-cells obtained from the spleen and other immunological organs of an experimental non-human animal, such as mouse, hamster and rabbit. For rabbit-blood derived B-cells 0.2% of $IgG^+$-cells were found after depletion of macrophages. Peyer'sche plaques from rabbit showed 0.4% of $IgG^+$-cells and spleen showed 0.3% of $IgG^+$-cells after depletion of macrophages.

With the methods as reported herein after about seven (7) days, i.e. after 5, 6, 7, or 8 days, especially after 7 or 8 days, of co-cultivation antibody concentrations of from about 30 ng/ml up to 15 µg/ml or more can be obtained (average value about 500 ng/ml). With the thereby provided amount of antibody a high number of different analyses can be performed in order to characterize the antibody, e.g. regarding binding specificity, in more detail. With the improved characterization of the antibody at this early stage in the screening/selection process it is possible to reduce the number of required nucleic acid isolations and sequencing reactions that have to be performed. Additionally the B-cell clone provides an amount of mRNA encoding monoclonal light and heavy chain variable region allowing the use of degenerated PCR primer and obviates the requirement of highly specific primer. Also the required number of PCR cycles is reduced. Thus, in one embodiment the reverse transcriptase PCR is with degenerated PCR primer for the light and heavy chain variable domain.

The co-cultivation step with feeder cells can be preceded and also succeeded by a number of additional steps.

In one embodiment of all methods as reported herein the feeder mix is a thymocyte cultivation supernatant. In a specific embodiment the thymocyte cultivation supernatant is obtained from the thymocytes of the thymus gland of the respective non-human animal.

Due to the origin of the feeder mix, which is derived from the supernatant of cultivated thymocytes (thymocyte cultivation supernatant—TSN), considerable batch to batch variations may occur.

In order to overcome this variability a synthetic feeder mix consisting of synthetic components can be employed.

A synthetic feeder mix consisting of IL-1β (interleukin-1 beta), TNF-α (tumor necrosis factor alpha), IL-2 (interleukin-2) and IL-10 (interleukin-10) is known from Tucci, A., et al., J. Immunol. 148 (1992) 2778-2784.

The B-cell-species-specific additives for the synthetic feeder mix can result in increased amounts of secreted antibody by the respective B-cell clone. Concomitantly highly producing cells contain more mRNA which in turn facilitates the reverse transcription and sequencing of the encoding nucleic acid, e.g. with a redundant, non-specific primer set.

By the addition of SAC (*Staphylococcus aureus* strain Cowan's cells, a single SAC lot was used) the number of antibody secreting B-cells and the average IgG-concentration in the supernatant after co-cultivation can be increased. For the addition of SAC in the co-cultivation a concentration range can be defined as reduced as well as increased concentrations of SAC reduce the amount of secreted antibody.

In one embodiment of all methods as reported herein the synthetic feeder mix for the co-cultivation of murine B-cells comprises IL-1ß, IL-2, IL-10, TNF-α and BAFF. In one embodiment BAFF is added at a concentration of 5 ng/ml.

In one embodiment of all methods as reported herein the synthetic feeder mix for the co-cultivation of hamster B-cells comprises IL-1ß, IL-2, IL-10, TNF-α, IL-6 and SAC. In one embodiment IL-6 is added at a concentration of 10 ng/ml. In one embodiment SAC is added at a 1:75,000 ratio.

In the presence of EL-4 B5 feeder cells at least IL-1ß and TNFα are required for the co-cultivation of mouse, hamster and rabbit B-cells. IL-2 and IL-10 can be omitted for the co-cultivation of murine cells. Hamster B-cells can be cultivated in the absence of either IL-2 or IL-10. Rabbit B-cells can be cultivated in the absence of either IL-2 or IL-10 or IL-6.

In one embodiment IL-1β, TNF-α, IL-2, IL-10 and IL-21 are recombinant murine IL-1β, murine TNF-α, murine IL-2, murine IL-10, and murine IL-21.

In one embodiment BAFF is added at a concentration of 5 ng/ml. In one embodiment IL-6 is added at a concentration of 10 ng/ml. In one embodiment SAC is added at a 1:75,000 ratio.

The co-cultivation is in one embodiment of all methods as reported herein in polystyrene multi well plates with wells with a round bottom. The working volume of the wells is in one embodiment of all methods as reported herein of 50 µl to 250 µl. In one embodiment the wells are coated at least partially with a non-fibrous substrate prepared from a blend of polymer plastic resin and amphipathic molecules, wherein the amphipathic molecule comprises a hydrophilic moiety and a hydrophobic region, wherein the hydrophobic regions are anchored within the substrate and the hydrophilic moieties are exposed on the substrate. In one embodiment the amphipathic molecules are chosen from alkylamine ethoxylated, poly (ethylene imine), octyldecamine or mixtures thereof (see e.g. EP 1 860 181).

Characterization of Co-Cultivated Cells

For the (qualitative and quantitative) determination of secreted IgG after the co-cultivation generally all methods known to a person of skill in the art such as an ELISA can be used. In one embodiment of all methods as reported herein an ELISA is used.

Depending on the characterization results a B-cell clone can be obtained, i.e. selected. The term "clone" denotes a population of dividing and antibody secreting B-cells arising from/originating from a single B-cell. Thus, a B-cell clone produces a monoclonal antibody.

Isolation of mRNA, Cloning and Sequencing

From the B-cells the total mRNA can be isolated and transcribed in cDNA. With specific primers the cognate VH- and VL-region encoding nucleic acid can be amplified. Almost no identical sequences are obtained. The method provides for highly diverse antibodies binding to the same antigen.

The primers used for the amplification of the VH-encoding nucleic acid can be used for cDNA obtained from cells from the NMRI-mouse, the Armenian Hamster, the Balb/c-mouse as well as the Syrian hamster and the rabbit.

In one embodiment of all methods as reported herein the amino acid sequence is derived from the amplified VH-encoding nucleic acid and the exact start and end point is identified by locating the amino acid sequences of EVQL/QVQL (SE ID NO: 40 and 41) to VSS (VH-region) (SEQ ID NO: 42) and DIVM/DIQM (SEQ ID NO: 43 and 44) to KLEIK (VL-region) (SEQ ID NO: 45).

Also reported herein is a method for producing an antibody comprising the following steps:
a) providing a population of (mature) B-cells (obtained from the blood of an experimental non-human animal),
b) staining the cells of the population of B-cells with at least one fluorescence dye (in one embodiment with one to four, or two to four fluorescence dyes),
c) depositing single cells of the stained population of B-cells in individual containers (in one embodiment is the container a well of a multi well plate),
d) cultivating the deposited individual B-cells in the presence of feeder cells and a feeder mix (in one embodiment the feeder cells are EL-4 B5 cells, in one embodiment the feeder mix is natural TSN, in one embodiment the feeder mix is a synthetic feeder mix),
e) determining the binding specificity of the antibodies secreted in the cultivation of the individual B-cells,
f) determining the amino acid sequence of the variable light and heavy chain domain of specifically binding antibodies by a reverse transcriptase PCR and nucleotide sequencing, and thereby obtaining a monoclonal antibody variable light and heavy chain domain encoding nucleic acid,
g) introducing the monoclonal antibody light and heavy chain variable domain encoding nucleic acid in an expression cassette for the expression of an antibody,
h) introducing the nucleic acid in a cell,
i) cultivating the cell and recovering the antibody from the cell or the cell culture supernatant and thereby producing an antibody.

In one embodiment the non-human animal is selected from rat, mouse, hamster, rabbit, non-human primates, sheep, dog, cow, chicken, amphibians, and reptiles.

The Method as Reported Herein

The invention is based at least in part on the finding that it is advantageous to use EL4-B5 feeder cells in the co-cultivation with B-cells which have been obtained from a cultivation of EL4-B5 cells that has a (final) cell density of more than 500,000 cells/ml, especially in the range of 600,000 cells/ml up to 1,500,000 cells/ml.

One aspect as reported herein is a method for co-cultivating one or more B-cells comprising the step of
incubating the one or more B-cells with EL4-B5 cells, whereby the EL4-B5 cells have been obtained/are from a cultivation of EL4-B5 cells that has a cell density of from 600,000 cells/ml up to 1,500,000 cells/ml.

In one embodiment the cultivation of EL4-B5 cells has a cell density of 650,000 cells/ml up to 1,450,000 cells/ml.

In one embodiment the cultivation of EL4-B5 cells has a cell density of 650,000 cells/ml up to 825,000 cells/ml.

In one embodiment the cultivation of EL4-B5 cells has a cell density of 700,000 cells/ml up to 775,000 cells/ml.

In one embodiment the cultivation of EL4-B5 cells has a cell density of 1,400,000 cells/ml up to 1,500,000 cells/ml.

The method is exemplified in the following with two B-cell preparations expressing antibodies with different binding specificity.

In the first example B-cells obtained from a rabbit that had been immunized with human CDCP1 were used.

The B-cells obtained from the immunized rabbit were deposited as single cells in the wells of a multi-well plate (for each three 96-well plates; 252 wells per each EL4-B5 cell density). Each single deposited cell was co-cultivated with 50,000 EL4-B5 cells irradiated with 50 gray in the presence of TSN and SAC for 7 days.

The average frequency of IgG positive wells, i.e. the wells in which IgG could be detected in the co-cultivation supernatant, was comparable irrespective of the cell density of the cultivation from which the EL4-B5 cells were taken (see following Table).

TABLE

| EL4-B5 cultivation cell density [×1000/ml] | 285 | 435 | 535 | 655 | 775 |
|---|---|---|---|---|---|
| IgG positive wells per plate [%] | 49.6 | 42.4 | 39.7 | 38.9 | 42.1 |

Also the average productivity was comparable irrespective of the cell density of the cultivation from which the EL4-B5 cells were taken (see following Table).

TABLE

| EL4-B5 cultivation cell density [×1000/ml] | 285 | 435 | 535 | 655 | 775 |
|---|---|---|---|---|---|
| average IgG concentration per plate [µg/ml] | 1.2 | 1.0 | 1.1 | 1.5 | 0.9 |

The average frequency of antigen-specific IgG positive wells, i.e. the wells in which IgG was produced that specifically binds to the target antigen, of the total wells was comparable only for low and high cell densities of the cultivation from which the EL4-B5 cells were taken (see following Table).

TABLE

| EL4-B5 cultivation cell density [×1000/ml] | 285 | 435 | 535 | 655 | 775 |
|---|---|---|---|---|---|
| antigen-specific IgG wells per plate [% total wells] | 24.6 | 13.5 | 15.9 | 25.4 | 28.6 |

The average frequency of antigen-specific IgG positive wells, i.e. the wells in which IgG was produced that specifically binds to the target antigen, of the IgG positive wells was comparable only for the high cell densities of the cultivation from which the EL4-B5 cells were taken (see following Table and FIG. 1).

TABLE

| EL4-B5 cultivation cell density [×1000/ml] | 285 | 435 | 535 | 655 | 775 |
|---|---|---|---|---|---|
| antigen-specific IgG wells per plate [% IgG-positive wells] | 51.5 | 32.6 | 39.2 | 65.6 | 68.6 |

In the second example B-cells obtained from a rabbit that had been immunized with human serum albumin were used.

The B-cells obtained from the immunized rabbit were deposited as single cells in the wells of a multi-well plate (for each two 96-well plates; 168 wells per each EL4-B5 cell density). Each single deposited cell was co-cultivated with 50,000 EL4-B5 cells irradiated with 50 gray in the presence of TSN and SAC for 7 days.

The average frequency of IgG positive wells, i.e. the wells in which IgG could be detected in the co-cultivation supernatant, was comparable up to a cell density of 1,450,000 cells/ml in the cultivation from which the EL4-B5 cells were taken (see following Table).

TABLE

| EL4-B5 cultivation cell density [×1000/ml] | 295 | 510 | 700 | 1100 | 1450 | 1710 | 2275 |
|---|---|---|---|---|---|---|---|
| IgG positive wells per plate [%] | 70.3 | 61.3 | 65.5 | 67.3 | 53.0 | 38.1 | 55.4 |

Also the average productivity was comparable up to a cell density of 1,450,000 cells/ml in the cultivation from which the EL4-B5 cells were taken (see following Table).

TABLE

| EL4-B5 cultivation cell density [×1000/ml] | 295 | 510 | 700 | 1100 | 1450 | 1710 | 2275 |
|---|---|---|---|---|---|---|---|
| average IgG concentration per plate [µg/ml] | 4.8 | 4.1 | 4.4 | 3.9 | 3.8 | 2.3 | 2.1 |

The average frequency of antigen-specific IgG positive wells, i.e. the wells in which IgG was produced that specifically binds to the target antigen, of the total wells was comparable up to a cell density of 1,450,000 cells/ml in the cultivation from which the EL4-B5 cells were taken (see following Table).

TABLE

| EL4-B5 cultivation cell density [×1000/ml] | 295 | 510 | 700 | 1100 | 1450 | 1710 | 2275 |
|---|---|---|---|---|---|---|---|
| antigen-specific IgG wells per plate [% total wells] | 23.8 | 20.3 | 26.2 | 23.2 | 21.5 | 8.4 | 7.8 |

Figure 2:
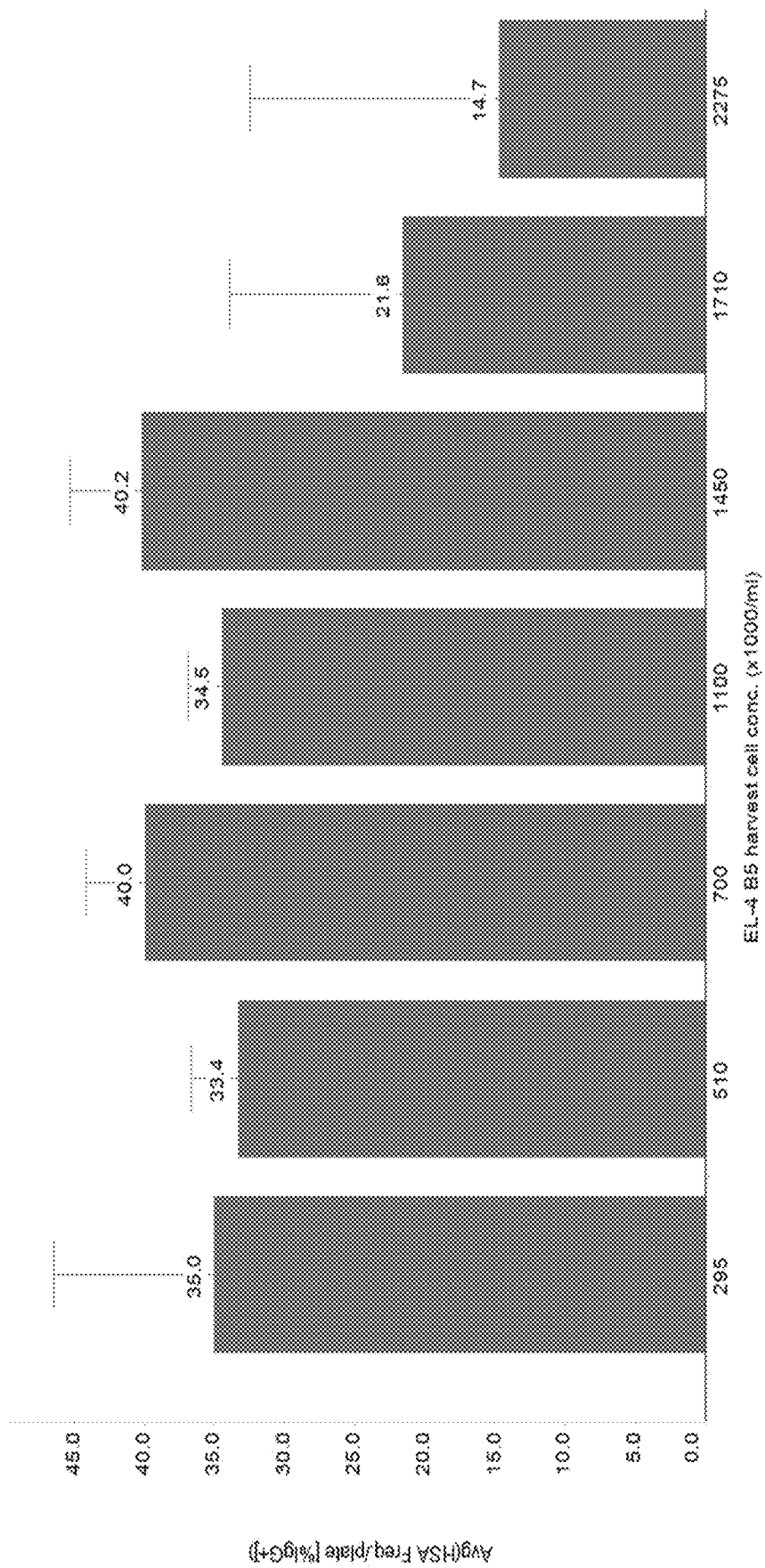
FIG. 2 Average frequency of antigen-specific IgG positive wells per IgG positive wells.

The average frequency of antigen-specific IgG positive wells, i.e. the wells in which IgG was produced that specifically binds to the target antigen, of the IgG positive wells was increased at cell densities of about 700,000 cells/ml and of about 1,450,000 cells/ml in the cultivation from which the EL4-B5 cells were taken (see following Table and FIG. 2).

TABLE

| EL4-B5 cultivation cell density [×1000/ml] | 295 | 510 | 700 | 1100 | 1450 | 1710 | 2275 |
|---|---|---|---|---|---|---|---|

TABLE-continued

| | | | | | | | |
|---|---|---|---|---|---|---|---|
| antigen-specific IgG wells per plate [% IgG-positive wells] | 35.0 | 33.2 | 40.0 | 34.5 | 40.2 | 21.6 | 14.7 |

The following examples and sequences are provided to aid the understanding of the present invention, the true scope of which is set forth in the appended claims. It is understood that modifications can be made in the procedures set forth without departing from the spirit of the invention.

EXAMPLES

Materials and Methods

Recombinant DNA Techniques

Standard methods were used to manipulate DNA as described in Sambrook, J., et al., Molecular Cloning: A Laboratory Manual, Cold Spring Harbor Laboratory Press, Cold Spring Harbor, N.Y. (1989). The molecular biological reagents were used according to the manufacturer's instructions.

Media and Buffers

Blocking buffer for ELISA comprises 1×PBS and 1% BSA.

Coating buffer for ELISA comprises 4.29 g Na2CO3*10 H2O and 2.93 g NaHCO3 add water to a final volume of 1 liter, pH 9.6 adjusted with 2 N HCl.

Ethanol-solution for RNA isolation comprises 70% Ethanol or 80% Ethanol.

FACS-buffer for immuno fluorescence staining comprises 1×PBS and 0.1% BSA.

IMDM-buffer for ELISA comprises 1×PBS, 5% IMDM and 0.5% BSA.

Incubation buffer 1 for ELISA comprises 1×PBS, 0.5 CroteinC.

Incubation buffer 2 for ELISA comprises 1×PBS, 0.5 CroteinC and 0.02% Tween 20.

Incubation buffer 3 for ELISA comprises 1×PBS, 0.1% BSA.

Incubation buffer 4 for ELISA comprises 1×PBS, 0.5% BSA, 0.05% Tween, PBS (10×), 0.01 M KH2PO4, 0.1 M Na2HPO4, 1.37 M NaCl, 0.027 M KCl, pH 7.0.

PCR-buffer comprises 500 mM KCl, 15 mM MgCl2, 100 mM Tris/HCl, pH 9.0.

Wash buffer 1 for ELISA comprises 1×PBS, 0.05 Tween 20.

Wash buffer 2 for ELISA comprises 1×PBS, 0.1% Tween 20.

Wash buffer 3 for ELISA comprises water, 0.9% NaCl, 0.05 Tween 20.

EL-4 B5 medium comprises RPMI 1640 (Pan Biotech, Aidenbach, Germany) supplemented with 10% FCS (Hyclone, Logan, Utah, USA), 2 mM Glutamine, 1% penicillin/streptomycin solution (PAA, Pasching, Austria), 2 mM sodium pyruvate, 10 mM HEPES (PAN Biotech, Aidenbach, Germany) and 0.05 mM β-mercaptoethanol (Gibco, Paisley, Scotland).

Animal Care and Immunization

The experimental animals were held according to the German animal protection law (TierSCHG) as well as according to the respective European guidelines.

The antigen was at first applied together with complete Freud's adjuvant (CFA). Further applications were with incomplete Freud's adjuvant (IFA). The antigen containing emulsion was applied subcutaneously whereby the emulsion comprised an amount of from 50 to 100 µg antigen depending on the weight of the receiving experimental animal.

NZW rabbits (Charles River Laboratories International, Inc.) were used for immunization. The antigen was solved in $K_3PO_4$ buffer pH 7.0 at a concentration of 1 mg/ml and mixed (1:1) with complete Freud's adjuvant (CFA) till generation of stabile emulsion. The rabbits received an intra dermal (i.d.) injection of 2 ml of emulsion followed by a second intra muscular (i.m.) and third subcutaneous (s.c.) injection each with 1 ml in one week interval. The fourth i.m. injection of 1 ml was performed two weeks later followed by two further s.c. injections of 1 ml in four weeks interval.

During the immunization serum antibody titer was determined with an antigen specific assay. At an antibody titer with an $IC_{50}$ of 1:10000 the blood or the spleen of the immunized animal was removed. For reactivation of antigen specific B-cells 30 µg to 50 µg of the antigen was applied intravenously to the experimental animal three days prior to the removal of the blood or the spleen.

Removal of Organs, Blood and Macrophages

Blood from mice and hamster was obtained by punctuation of the retrobulberic vein. Blood from rabbits was obtained by punctuation of the ear vein or, for larger volumes, of the ear artery. Whole blood (10 ml) was collected from rabbits 4-6 days after the third, fourth, fifth and sixth immunization and used for single cell sorting by FACS.

Macrophages were isolated from the obtained blood by attachment to cell culture plastic. From mice and hamsters, about $3*10^5$ macrophages can be obtained from each animal by this method.

If a larger amount of mouse or hamster macrophages was required, peritoneal macrophages were isolated. For this the animals have to be at least 3 months of age. For the removal of peritoneal macrophages, animals were sacrificed and 5 ml of EL-4 B5 medium with a temperature of 37° C. was immediately injected into the peritoneal cavity. After kneading the animal's belly for 5 minutes, the solution containing the cells was removed.

EDTA containing whole blood was diluted twofold with 1×PBS before density centrifugation on lympholyte mammal (Cedarlane Laboratories) or Ficoll Paque Plus (GE Healthcare, cat. #17-1440-03), which was performed to isolate rabbit PBMC. PBMCs were washed twice before staining with antibodies.

Density Gradient Centrifugation

The isolation of peripheral blood mononuclear cells (PBMCs) was effected by density gradient separation with Lympholyte® according to manufacturer's instructions A (Lympholyte®-mammal, Cedarlane).

Withdrawn blood was diluted 2:1 with phosphate buffered saline (PBS). In a centrifuge vial the same volume of density separation medium was provided and the diluted blood is carefully added via the wall of the vial. The vial was centrifuged for 20 min. at 800×g without braking. The lymphocytes were obtained from the white interim layer. The removed cells were supplemented with 10 ml PBS and centrifuged at 800×g for 10 min. The supernatant was discarded and the pellet was resuspended, washed, centrifuged. The final pellet was resuspended in PBS.

Hypotonic Lysis of Red Blood Cells

For disruption of red blood cells by hypotonic lysis an ammonium chloride solution (BD Lyse™) was diluted 1:10 with water and added at a ratio of 1:16 to whole blood. For lysis of the red blood cells the mixture was incubated for 15 min. in the dark. For separation of cell debris from intact cells the solution was centrifuged for 10 min. at 800×g. The supernatant was discarded, the pellet was resuspended in PBS, washed again, centrifuged and the pellet was resuspended in PBS. Example 8

Depletion of Macrophages

Sterile 6-well plates (cell culture grade) were used to deplete macrophages and monocytes through unspecific adhesion. Wells were either coated with KLH (keyhole limpet haemocyanine) or with streptavidin and the control peptides. Each well was filled with 3 ml to (at maximum) 4 ml medium and up to $6 \times 10^6$ peripheral blood mononuclear cells from the immunized rabbit and allowed to bind for 60 to 90 min. at 37° C. in the incubator. Thereafter the lymphocyte containing supernatant was transferred to a centrifugation vial and centrifuged at 800×g for 10 min. The pellet was resuspended in PBS.

Enrichment of Antigen-Specific B-Cells

The respective antigen was diluted with coating buffer to a final concentration of 2 µg/ml. 3 ml of this solution were added to the well of a 6-well multi well plate and incubated over night at room temperature. Prior to use the supernatant was removed and the wells were washed twice with PBS. The B-cell solution was adjusted to a cell density of $2 \times 10^6$ cells/ml and 3 ml are added to each well (up to $6 \times 10^6$ cells per 3-4 ml medium) of a 6-well multi well plate. The plate was incubated for 60 to 90 min. at 37° C. The supernatant was removed and non-adherent cells were removed by carefully washing the wells 1-4 times with 1×PBS. For recovery of the sticky antigen-specific B-cells 1 ml of a trypsin/EDTA-solution was added to the wells of the multi well plate and incubated for 10 to 15 min. at 37° C. The incubation was stopped by addition of medium and the supernatant was transferred to a centrifugation vial. The wells were washed twice with PBS and the supernatants were combined with the other supernatants. The cells were pelleted by centrifugation for 10 min. at 800×g. The cells were kept on ice until the immune fluorescence staining. The pellet was optionally resuspended in PBS.

Co-Cultivation of B-cells and EL-4 B5 Cells a) The co-cultivation was performed in 96-well multi well plates with round bottom. A basis solution comprising EL-4 B5 cells ($1.6 \times 10^6$ cells/15.2 ml) and cytokines in EL-4 B5 medium was prepared. 200 µl of the basis solution was added to each well of the multi well plate. To each well a single B-cell was added by fluorescence activated cell sorting. After the addition of the B-cells the plate was centrifuged for 5 min. at 300×g. The plate is incubated for seven days at 37° C.

b) Single sorted B-cells were cultured in 96-well plates with 210 µl/well EL-4 B5 medium with Pansorbin Cells (1:20000) (Calbiochem (Merck), Darmstadt, Deutschland), 5% rabbit thymocyte supernatant and gamma-irradiated EL-4-B5 murine thymoma cells ($2 \times 10^4$/well) for 7 days at 37° C. in an atmosphere of 5% $CO_2$ in the incubator. B-cell culture supernatants were removed for screening and the cells harvested immediately for variable region gene cloning or frozen at −80° C. in 100 µl RLT buffer (Qiagen, Hilden, Germany).

Human B-cells were cultured accordingly.

Cultivation of T-Cells

The T-cells were isolated from the thymus of 3-4 week old mice and hamsters, or of 4-5 week old rabbits, respectively. The cells were centrifuged and immediately cultivated or frozen in aliquots of $3 \times 10^7$ cells. The thymocytes were seeded with a minimum cell density of $5 \times 10^5$ cells/ml of EL-4 B5 medium in 175 cm² culture flasks and incubated for 48 hours at 37° C.

Cultivation of Macrophages

Macrophages were isolated from the peritoneal cavity of mice and hamsters, respectively, of an age of at least three months. Peritoneal macrophages from mice or hamsters, or blood mononuclear cells from rabbits were cultivated in EL-4 B5 medium at a cell density of at least $1 \times 10^5$ cells/ml in 175 cm² culture flasks for 1.5 hours at 37° C. Afterwards the medium was removed and non-attached cells were removed from the attached macrophages by washing with warm EL-4 B5 medium, followed by cultivation for 48 hours in 35 ml medium.

Co-Cultivation of T-Cells and Macrophages

T-cells and macrophages were cultivated for 48 hours in separate flasks. Prior to combining both cell populations, the T-cells were centrifuged for 10 min. at 800×g. The supernatant was discarded and the cell pellet was resuspended in 10 ml medium. The T-cells were adjusted to a minimal cell density of $5 \times 10^5$ cells/ml and 10 pg phorbol-12-myristate-13-acetate (PMA) and 5 ng or 50 ng Phytohemagglutinin M (PHA-M) per ml of medium were added. The cultivation medium was removed from macrophages and the T-cell suspension was added to the flasks containing macrophages. After 36 hours of co-cultivation, the cultivation medium was removed and was termed TSN solution. For removal of remaining cells the TSN solution was filtered through a 0.22 µm filter. The TSN solution was frozen at −80° C. in aliquots of 4 ml.

Immunofluorescence Staining

Protocol 1:

Depending on the number of cells to be stained the cells were provided in 100 µl medium (less than $10^6$ cells) or 200 µl medium (more than $10^6$ cells), respectively. The fluorescent labeled antibody was diluted with 5% serum of the experimental animal and FACS buffer to a final volume of 100 µl or 200 µl, respectively. The reaction mixture was incubated on a roller rack for 40 min. at 4° C. in the dark. After the incubation the cells were washed twice at 300×g for 5 min. The pellet was resuspended in 400 µl PBS and filtered through a 70 µm sieve. The filtered solution was transferred to a FACS-vial and directly before the FACS experiment dead cells were stained by addition of propidium iodide (6.25 µg/ml). If the labeled antibody was labeled with biotin the antibody was detected in a second step with streptavidin labeled Alexa Flour(R) 647 (antibody 197).

Protocol 2:

Anti-rabbit IgG FITC used for single cell sorting was from AbD Serotec (STAR121F, Düsseldorf, Germany).

For surface staining, cells were incubated with the optimally diluted anti-rabbit IgG FITC antibody in PBS for 30 min. with rolling at 4° C. in the dark. Following centrifugation, the supernatants were removed by aspiration. The PBMCs were subjected to two cycles of centrifugation and washing with ice cold PBS. Finally the PBMCs were resuspended in ice cold PBS and immediately subjected to the FACS analyses. Propidium iodide in a concentration of 5 µg/ml (BD Pharmingen, San Diego, Calif., USA) was added prior to the FACS analyses to discriminate between dead and live cells. In other experiments the stained cells were single deposited by FACS.

A Becton Dickinson FACSAria equipped with a computer and the FACSDiva software (BD Biosciences, USA) were used to collect and analyze the data.

Proliferation Assays a) Cell Titer Glo (CTG) viability assay

The CTG viability assay (Promega; # G7571) was used according to the instructions of the manufacturer.

b) $^3$H Thymidine Assay

After 6 days of incubation $^3$H-Thymidin was added (0.5 µCi/well) and incubated for further 16 hours. The incorporation of $^3$H-Thymidine during cell proliferation was determined with a microplate scintillation counter (Wallac).

c) Microscopic Analysis

For the acquisition of microscopic images, a phase contrast microscope from Leica (Leica DM IL) combined with a high resolution camera (Leica DFC290 HD) was used.

d) Analysis of B-cell activation via CFSE-labeling.

Isolated B-cells were washed with sterile phosphate buffer saline solution (PBS). Up to $1 \times 10^7$ cells were resuspended in 1 ml protein-free PBS and incubated with CFSE (# C34554, Invitrogen/Molecular Probes) for 3 to 10 minutes at a final concentration of 2.5 µM at 37° C. CFSE loading was stopped by addition of an excess of FCS-supplemented medium. After extensive washing with FCS-containing medium, B-cells were used in co-culture experiments. Proliferation of $CD19^+$ gated (B-)cells as a consequence of CFSE dilution was confirmed by flow cytometric analysis (FL-1 channel) after indicated time points.

Quantification of IgG

The 96-well multi well plate in which the co-cultivation was performed was centrifuged after seven days of co-cultivation at 300×g for 5 min. 150 µl supernatant was removed and diluted at a ratio of 2:1 with PBS in a second 96-well multi well plate.

The antibody was used at a concentration of 50 ng/ml. If the OD was or exceeded 1 after an incubation time of 5 min. a dilution series of from 0.8 to 108 ng/ml IgG was tested.

Detection of Antigen-Specific IgG

Antibodies produced by single deposited and co-cultivated B-cells or from B-cells obtained from an immunized experimental animal can be characterized with respect to specific antigen binding. The ELISA was performed at room temperature and the ELISA-solution was incubated between the individual steps on a shaker at 20×g. In the first step the antigen was bound to the wells of a 96-well multi well plate. If the antigen was a protein it had been diluted in coating buffer and applied directly to the plate. Peptide antigens were bound via the specific binding pair biotin/streptavidin. The wells of the multi well plate can be already coated with soluble CroteinC (CrC) by the manufacturer. If not, the wells were incubated after the immobilization of the antigen with 200 µl blocking buffer. After the incubation with 100 µl antigen solution per well (pre-coated multi well plate) or 200 µl blocking buffer, respectively, non-bound antigen or blocking buffer was removed by washing with wash buffer. The diluted B-cell supernatants were added in a volume of 100 µl per well and incubated. After the incubation the wells were washed. Afterwards the detection antibody was added in a volume of 100 µl per well. The antibody can be either conjugated to horseradish peroxidase or labeled with biotin. The detection antibody was determined with a streptavidin-horseradish peroxidase conjugate. After the incubation the multi well plate was washed and afterwards 50 µl of a substrate solution containing 3,3',5,5' tetramethyl benzidine (TMB) were added per well and incubated for a period as given in Table X. The enzymatic reaction was stopped by the addition of 50 µl sulfuric acid and the optical density was determined at 450 nm and 680 nm with a photometer (Rainbow Thermo ELISA Reader) and the Xread plus-software.

Isolation of Ribonucleic Acid (RNA)

The cells from which the RNA had to be isolated were at first pelleted by centrifugation. The cell pellet was lysed by the addition of 100 µl RLT-buffer with 10 µl/ml beta-mercaptoethanol. The cells were resuspended by multiple mixing with a pipette. The solution was transferred to a well of a multi well plate. The plate was shortly shock at 200×g and frozen at −20° C.

The isolation of the RNA was performed with the RNeasy® Kit (Qiagen, Hilden, Germany) according to the manufacturer's instructions.

Reverse Transcription Polymerase Chain Reaction

Protocol 1:

The reverse transcription was carried out in a volume of 20 µl. For each reaction a control was performed with and without reverse transcriptase. Per reaction 1 µl dNTP (each at 10 mM), 0.4 µl oligo(dT)$_{12-18}$ (0.2 µg) and 0.6 µl random hexamer (0.03 µg) were pre-mixed and added to 8.5 µl RNA in H2O. The reaction mixture was incubated for 5 min. at 65° C. and directly afterwards transferred to ice. Thereafter 2 µl RT-buffer (10×), 4 µl MgCl2 (25 mM), 2 µl DTT (0.1 M) and 1 µl RNAse Out™ (40 units) were pre-mixed and added to the ice cold reaction mixture. After an incubation time of 2 min. at room temperature 0.5 µl Superscript™ II reverse transcriptase (25 units) were added. The reaction mixture was incubated for 10 min. at room temperature. The translation was carried out for 50 min. at 42° C. After the translation the reverse transcriptase was inactivated by incubation for 15 min. at 70° C. The cDNA was stored at −20° C.

Protocol 2:

cDNA was generated by reverse transcription of mRNA using the Super Script III first-strand synthesis SuperMix (Invitrogen) according to the manufacturer's instructions. In a first step 6 µl of the isolated mRNA was mixed with 1 µl annealing buffer and 1 µl (50 µM) oligo dT, incubated for 5 minutes at 65° C. and thereafter immediately placed on ice for about 1 minute. Subsequently while still on ice 10 µl 2× First-Strand Reaction Mix and SuperScript™ III/RNase-OUT™ Enzyme Mix were added. After mixing the reaction was incubated for 50 minutes at 50° C. The reaction was terminated by incubation at 85° C. for 5 minutes. After termination the reaction mix was placed on ice.

Polymerase Chain Reaction

Protocol 1:

The polymerase chain reaction was carried out with the Taq PCR Core Kit (Qiagen, Hilden, Germany) according to the manufacturer's instructions. The PCR was carried out in a volume of 20 µl. The samples were transferred to the Mastercyler® at a temperature of 95° C.

Protocol 2:

The polymerase chain reaction was carried out using AccuPrime Pfx SuperMix (Invitrogen) according to the manufacturer's instructions. Light chain and heavy chain variable regions were amplified in separate reactions. PCR-primer (0.2 µM/reaction) with 25 bp overlaps to target antibody expression vectors were used. After the PCR 8 µl of the PCR reaction mixture were used for analysis on 48-well eGels (Invitrogen).

Sequencing

DNA sequences were determined by double strand sequencing performed at SequiServe GmbH (Vaterstetten, Germany).

DNA and Protein Sequence Analysis and Sequence Data Management

The GCG's (Genetics Computer Group, Madison, Wis.) software package variant 10.2 and Infomax's Vector NTI Advance suite variant 8.0 was used for sequence creation, mapping, analysis, annotation and illustration.

Gene Synthesis

Desired gene segments encoding cDNA were prepared by Geneart GmbH (Regensburg, Germany). The gene segments are flanked by singular restriction endonuclease cleavage sites to facilitate expression construct cloning as described below. The DNA sequence of the subcloned gene fragments were confirmed by DNA sequencing.

Panning on Antigen a) Coating of Plates

Biotin/Streptavidin: Sterile streptavidin-coated 6-well plates (cell culture grade) were incubated with biotinylated antigen at a concentration of 0.5-1(2) µg/ml in PBS at room temperature for one hour. Plates were washed in sterile PBS three times before use.

Covalently bound protein: Sterile cell culture 6-well plates were coated with 2 µg/ml protein in carbonate buffer (0.1 M sodium bicarbonate, 34 mM disodium hydrogen carbonate, pH 9.55) over night at 4° C. Plates were washed in sterile PBS three times before use.

b) Panning of B-Cells on Antigen 6-well tissue culture plates coated with the respective antigen were seeded with up to $6 \times 10^6$ cells per 4 ml medium and allowed to bind for one hour at 37° C. in the incubator. Non-adherent cells were removed by carefully washing the wells 1-2 times with 1×PBS. The remaining sticky cells were detached by trypsin for 10 min. at 37° C. in the incubator and then washed twice in media. The cells were kept on ice until the immune fluorescence staining.

Preparation of Plasmid-DNA

The plasmid DNA to be used as recipient for the cloning of the PCR products encoding the antibody heavy and light chain variable domains was first linearized by restriction enzyme digestion. Subsequently, the linearized plasmid DNA was purified by preparative agarose electrophoresis and extracted from the gel (QIAquick Gel Extraction Kit/Qiagen). This purified plasmid DNA was added to a PCR-protocol as template using primer overlapping (by 20-25 bp) with the PCR-products to be cloned. The PCR was carried out using AccuPrime Pfx SuperMix (Invitrogen).

Cloning

The PCR-products were cloned into expression vectors using a "site and ligation independent cloning" method (SLIC) which was described by Haun, R. S., et al. (BioTechniques 13 (1992) 515-518) and Li, M. Z., et al. (Nature Methods 4 (2007) 251-256). Both purified vector and insert were treated with 0.5 U T4 DNA polymerase (Roche Applied Sciences, Mannheim, Germany) per 1 µg DNA for 45 minutes at 25° C. in the absence of dNTPs to generate matching overhangs. The reaction was stopped by adding $\frac{1}{10}^{th}$ of the reaction volume of a 10 mM dCTP Solution (Invitrogen). The T4 treated vector and insert DNA fragments were combined with a plasmid:insert ratio of 1:2 (w/w) (e.g. 100 ng:200 ng) and recombined by adding RecAProtein (New England Biolabs) and 10×RecA Buffer for 30 minutes at 37° C. Subsequently, 5 µl of each of the generated heavy chain and light chain expression plasmid was used to transform MultiShot Strip Well TOP 10 Chemically Competent *E. coli* cells (Invitrogen) using a standard chemical transformation protocol. After regeneration (shaking for 45 minutes at 37° C. of the transformed *E. coli* cells) the entire transformation mixture was transferred into DWP 96 (deep well plates) containing 2 ml of LB medium supplemented with ampicillin per well. The cells were incubated in a shaker for 20 hours at 37° C. In the following step the plasmid DNA encoding the immunoglobulin heavy- and light chains was purified using the NucleoSpin 96 Plasmid Mini Kit (Macherey&Nagel), digested with selected restriction enzymes, and analyzed on 48-well eGels (Invitrogen). In parallel, glycerol stocks were prepared for storage.

Transfection and Expression of Recombinant Antibodies in Eukaryotic Cells

HEK293 cells were grown with shaking at 120 rpm in F17-medium (Gibco) at 37° C. in an atmosphere containing 8% $CO_2$. Cells were split the day before transfection and seeded at a density of $0.7-0.8 \times 10^6$ cells/ml. On the day of transfection, $1-1.5 \times 10^6$ HEK293 cells in a volume of 2 ml were transfected with 0.5 µg HC plasmid plus 0.5 µg LC plasmid, suspended in 1 µl 293-free medium (Novagen) and 80 µl OptiMEM® medium (Gibco) in 48 well deep well plates. Cultures were incubated for 7 days at 180 rpm at 37° C. and 8% $CO_2$. After 7 days the culture supernatants were harvested, filtered and analyzed for antibody content and specificity.

Primer a) Primer for B-cell PCR of B-cells expressing rabbit antibodies

```
primer set 1:
LC-primer
-rb-V-kappa-HindIIIs (SEQ ID NO: 01):
GATTAAGCTTATGGACAYGAGGGCCCCCACTC -rb-C-kappa-NheIas (SEQ ID NO: 02):
GATCGCTAGCCCTGGCAGGCGTCTCRCTCTAACAG HC-primer
-rb-CH1rev-1 (SEQ ID NO: 03):
GCAGGGGGCCAGTGGGAAGACTG -rbVH3-23for3 (SEQ ID NO: 04):
CACCATGGAGACTGGGCTGCGCTGGCTTC primer set 2:
LC-primer
-rb-V-kappa-Slic-s001 (SEQ ID NO: 06):
AAGCTTGCCACCATGGACAYGAGGGCCCCCACTC
```

-rbCk1-rev2 (SEQ ID NO: 07):
CAGAGTRCTGCTGAGGTTGTAGGTAC

HC-primer
-rb-VH3-23-Slic-s001 (SEQ ID NO: 08):
AAGCTTGCCACCATGGAGACTGGGCTGCGCTGGCTTC -rb-CH1rev-2 (SEQ ID NO: 09):
CCATTGGTGAGGGTGCCCGAG primer for amplification of heavy chain expression plasmid backbone:
-8001-Slic-s001 (SEQ ID NO: 10):
TGGGAACTCGGGCACCCTCACCAATGG -8001-Slic-as002 (SEQ ID NO: 11):
GCCCAGTCTCCATGGTGGCAAGCTTCCTCTGTGTTCAGTGCTG primer for amplification of kappa light chain expression plasmid backbone:
-8011-Slic-s001 (SEQ ID NO: 12):
GTACCTACAACCTCAGCAGCACTCTG -8000-Slic-as002 (SEQ ID NO: 13):
CCCTCRTGTCCATGGTGGCAAGCTTCCTCTGTGTTCAGTGCTG b) Primer for B-cell PCR of rabbit B-cells expressing human antibodies
(derived from transgenic rabbit)
primer for amplification of heavy chain variable domains
HC-Up
-rb-VH3-23-Slic-s001 (SEQ ID NO: 08):
AAGCTTGCCACCATGGAGACTGGGCTGCGCTGGCTTC -bcPCR-huCgamma-rev (SEQ ID NO: 05):
CCCCCAGAGGTGCTCTTGGA primer for amplification of light chain variable domains
-bcPCR-FHLC-leader-fw (SEQ ID NO: 06):
ATGGACATGAGGGTCCCCGC -bcPCR-huCkappa-rev (SEQ ID NO: 07):
GATTTCAACTGCTCATCAGATGGC c) Primer for the amplification of heavy chain plasmid backbone:
-bcPCR-hu-HC-10600-SLIC-as (SEQ ID NO: 08):
CAGCCCAGTCTCCATGGTGGCAAGCTTCCTCTGTGTTCAGTGCTG -bcPCR-hu-HC-10600-SLIC-s (SEQ ID NO: 09):
CTCCAAGAGCACCTCTGGGGGCACAG d) Primer for the amplification of kappa light chain plasmid backbone:
-bcPCR-hu-LC-10603-SLIC-s (SEQ ID NO: 10):
GCCATCTGATGAGCAGTTGAAATC -bcPCR-hu-LC-10603-SLIC-as (SEQ ID NO: 11):
GCGGGGACCCTCATGTCCATGGTGGCAAGCTTCCTCTG e) Primer for B-cell PCR of B-cells from human donors primer for amplification
of heavy chain variable domains
-SLIC-hu-VHuniversal-for (SEQ ID NO: 12):
AGCAACAGCTACAGGTGTGCATTCCGAGGTGCAGCTGKTGSAG
TCTGS -SLIC-hu-VH6-for (SEQ ID NO: 13):
AGCAACAGCTACAGGTGTGCATTCCCAGGTRCAGCTGCAGSAG
TC -hu-CH1gamma-rev (SEQ ID NO: 14):
GTCCACCTTGGTGTTGCTGGGCTT Primer for amplification of kappa light chain variable domains
-SLIC-huVk2-for (SEQ ID NO: 15):
TAGCAACAGCTACAGGTGTGCATTCCGATGTTGTGATGACTCAG
TCT -SLIC-huVk3-for (SEQ ID NO: 16):
TAGCAACAGCTACAGGTGTGCATTCCGAAATTGTGWTGACRCA
GTCT -SLIC-huVk5-for (SEQ ID NO: 17):
TAGCAACAGCTACAGGTGTGCATT CGACATCGTGATGACCCA
G -SLIC-huVk7-for (SEQ ID NO: 18):
TAGCAACAGCTACAGGTGTGCATTCCGAAATTGTGCTGACTCA
GTCT -SLIC-huVk8-for (SEQ ID NO: 19):
TAGCAACAGCTACAGGTGTGCATTCCGAWRTTGTGMTGACKCA
GTCTCC -SLIC-huVk1long-for (SEQ ID NO: 20):
TAGCAACAGCTACAGGTGTGCATTCCGACATCCRGWTGACCCA
GTCT -SLIC-huVk2longw-for (SEQ ID NO: 21):
TAGCAACAGCTACAGGTGTGCATTCCGATRTTGTGATGACYCA
GWCT -huCk-rev (SEQ ID NO: 22):
ACACTCTCCCCTGTTGAAGCTC Primer for amplification of lambda light chain variable domains
-SLIC-huVl1-for (SEQ ID NO: 23):
TAGCAACAGCTACAGGTGTGCATTCCCAGTCTGTGYTGACKCAG -SLIC-huVl2-for (SEQ ID NO: 24):
TAGCAACAGCTACAGGTGTGCATTCCCAGTCTGCCCTGACTCAG -SLIC-huVl3-for (SEQ ID NO: 25):
TAGCAACAGCTACAGGTGTGCATTCCTCCTATGAGCTGAYWCAG -SLIC-huVl4-for (SEQ ID NO: 26):
TAGCAACAGCTACAGGTGTGCATTCCCAGCYTGTGCTGACTCAA -SLIC-huVl5-for (SEQ ID NO: 27):
TAGCAACAGCTACAGGTGTGCATTCCCAGSCTGTGCTGACTCAG -SLIC-huVl6-for (SEQ ID NO: 28):
TAGCAACAGCTACAGGTGTGCATTCCAATTTTATGCTGACTCAG -SLIC-huVl7-for (SEQ ID NO: 29):
TAGCAACAGCTACAGGTGTGCATTCCCAGRCTGTGGTGACTCAG -SLIC-huVl8-for (SEQ ID NO: 30):
TAGCAACAGCTACAGGTGTGCATTCCCAGACTGTGGTGACCCAG -SLIC-huVl9-for (SEQ ID NO: 31):
TAGCAACAGCTACAGGTGTGCATTCCCWGCCTGTGCTGACTCAG -SLIC-huVlambda10-for (SEQ ID NO: 32):
TAGCAACAGCTACAGGTGTGCATTCCCAGGCAGGGCTGACTCAG -huCl-1-rev (SEQ ID NO: 33):
TCTCCACGGTGCTCCCTTC f) Primer for amplification of human immunoglobulin expression plasmid
amplification of heavy chain expression plasmid backbone:
-huIg-PCR-vectorprimer-as (SEQ ID NO: 34):
GGAATGCACACCTGTAGCTGTTGCTA -huIg-PCR-vectorprimer-VH-s (SEQ ID NO: 35):
AAGCCCAGCAACACCAAGGTGGAC amplification of kappa light chain expression plasmid backbone:
-huIg-PCR-vectorprimer-as kappa (SEQ ID NO: 36):
GGAATGCACACCTGTAGCTGTTGCTA -huIg-PCR-vectorprimer-VK-s (SEQ ID NO: 37):
GAGCTTCAACAGGGGAGAGTGT amplification of lambda light chain expression plasmid backbone:
-huIg-PCR-vectorprimer-as lambda (SEQ ID NO: 38):
GGAATGCACACCTGTAGCTGTTGCTA -huIg-PCR-vectorprimer-VL-s (SEQ ID NO: 39):
GAAGGGAGCACCGTGGAGA Cytokines Zubler Mix: 2 ng/ml mouse IL-1ß, 50 ng/ml mouse IL-2, 10 ng/ml mouse IL-10, and 2 ng/ml mouse TNFα (final concentration)

Cytokines tested for establishment of a defined cytokine cocktail (given as final concentration in case not stated otherwise):

| cytokine | final concentration | supplier | Catnr. |
|---|---|---|---|
| huIL-2 | 50 U/ml | Roche Dia. GmbH | 11147528001 |
| huIL-21 | 25 ng/ml | eBioscience | 14-8219 |
| muIL-21 | 100 ng/ml | R&Dsystems | 594-ML |
| huIL-6 | 300 U/ml | Roche Dia. GmbH | 11138600001 |
| huIL-10 | 25 ng/ml | BD | 554611 |
| huIL-1β | 12.5 ng/ml | R&Dsystems | 201-LB |
| huIL-33 | 100 ng/ml | Peprotech | 200-33 |
| TNFα | 25 ng/ml | R&Dsystems | 210-TA |

| Rabbit B-cell medium | | |
|---|---|---|
| 500 ml RPMI 1640 | #P04-17500 | PAN Biotech |
| 50 ml FCS | #A15-512 | PAA |
| 5 ml L-Gln | #25030-024 | Invitrogen |
| 5 ml potassium Pyruvate | #P04-43100 | PAN Biotech |
| 5 ml HEPES | #15630-056 | Invitrogen |
| 500 μl β-Mercaptoethanol | #31350010 | Invitrogen |
| 1 ml Pen/Strep | #11074440001 | Roche Dia. GmbH |

| Additives to rabbit B-cell medium | | |
|---|---|---|
| SAC | #507858 | Calbiochem |
| IL-21 | #14-8219 | eBioscience |
| IL-2 | #1114752800 | Roche |
| 96er U-plate | #3799 | Coming |

| Phenotyping/sorting of antibodies | | |
|---|---|---|
| goat anti-rabbit IgG Fc-antibody | AbDSerotec | STAR121F |
| rat anti-rabbit CD138-antibody | RocheGlycArt AG | |
| anti-human CD40 mAb (clone Mab89) | Beckman Coulter | IM1374 |
| anti human/murine (rabbit cross-reactive) | | |

| Phenotyping/sorting of antibodies | | |
|---|---|---|
| anti CD40L antibody: | | |
| anti-muCD40L antibody | R&D systems | AF1163 |
| anti-huCD40L antibody | &D systems | AF617 R |
| donkey anti-goat IgG antibody Alexa 488 | Molecular Probes | A11055 |

| Miscellaneous | | |
|---|---|---|
| anti-FITC antibody-coupled microbeads | Miltenyi Biotec | #130-048-701 |
| human B-cell negative isolation kit | Invitrogen | #113.13D |
| Nucleofector Kit T | Lonza | VCA-1002 |
| CBA for total IgG | BD Biosciences | #558679 |

Example 1

Cultivation of EL-4 B5 Cells

The frozen EL-4 B5 cells were thawed rapidly in a water bath at 37° C. and diluted with 10 ml EL-4 B5 medium. After centrifugation at 300×g for 10 minutes the supernatant was discarded and the pellet resuspended in 1 ml medium.

The EL-4 B5 cells were inoculated at a cell density of $8 \times 10$ cells/ml in T175 cultivation flasks. Cell density was determined every second day and adjusted to $8 \times 10^4$ cells/ml. The cells have a doubling time of approximately 18 hours. Afterwards cells were seeded with cell counts from $3 \times 10^4$ to $4 \times 10^5$ cells/ml to reach different final cell densities of up to $2275 \times 10^5$ cells/ml.

Cells were harvested and adjusted to a cell density of $1 \times 10^6$ cells/ml before γ-irradiation at 50 Gy.

Example 2

Co-Cultivation of B-Cells and EL-4 BS Cells

Single sorted B-cells were cultured in 96-well plates with 200 μl/well EL-4 B5 medium with Pansorbin Cells (1:100000) (Calbiochem (Merck), Darmstadt, Deutschland), 5% rabbit thymocyte supernatant and gamma-irradiated EL-4-B5 murine thymoma cells ($5 \times 10^4$/well) for 7 days at 37° C. in an atmosphere of 5% $CO_2$ in an incubator. B-cell culture supernatants were removed for screening and the cells harvested immediately for variable region gene cloning or frozen at −80° C. in 100 μl RLT buffer (Qiagen, Hilden, Germany).

The invention claimed is:

1. A method for co-cultivating one or more B-cells comprising the steps of
   cultivating EL4-B5 cells to a cell density of more than 1,000,000 cells/ml to 1,500,000 cells/ml, and
   incubating the one or more B-cells with an aliquot of the EL4-B5 cells obtained in the previous step.

2. The method according to claim 1, wherein the cultivation of the EL4-B5 cells is to a cell density of 650,000 cells/ml to 1,450,000 cells/ml.

3. The method according to claim 1, wherein the cultivation of the EL4-B5 cells is to a cell density of 1,400,000 cells/ml to 1,500,000 cells/ml.

4. The method according to claim 1, wherein the incubating is additionally in the presence of a feeder mix.

5. The method according to claim 4, wherein the feeder mix comprises one or more of:
   i) interleukin-1 beta and tumor necrosis factor alpha,
   ii) interleukin-2 (IL-2) and/or interleukin-10 (IL-10),
   iii) *Staphylococcus aureus* strain Cowan's cells (SAC),
   iv) interleukin-21 (IL-21) and optionally interleukin-2 (IL-2),
   v) B-cell activation factor of the tumor necrosis factor family (BAFF),
   vi) interleukin-6 (IL-6),
   vii) interleukin-4 (IL-4), and
   viii) thymocyte cultivation supernatant.

6. The method according to claim 4, wherein the feeder mix comprises IL-1ß, TNF-α, IL-10 and one or more of the members selected from the group consisting of: IL-21, SAC, BAFF, IL-2, IL-4, and IL-6.

7. The method according to claim 1, wherein the EL4-B5 cells are, after the cultivating and prior to the incubating, irradiated with γ-radiation.

8. The method according to claim 1, wherein the method is for the co-cultivation of one B-cell.

9. The method according to claim 8, wherein the one B-cell is a single deposited B-cell.

10. The method according to claim 1, wherein the incubating is for 5 to 14 days.

11. A method for producing an antibody, the method comprising performing the method according to claim 1, thereby producing the antibody.

12. The method according to claim 11, wherein the antibody is produced by the one or more B cells.

13. The method according to claim 12, wherein the antibody is produced by the one or more B cells and secreted into cell culture supernatant.

14. The method according to claim 12, further comprising recovering the antibody from the one or more B cells.

15. The method according to claim 13, further comprising recovering the antibody from the cell culture supernatant.

* * * * *